United States Patent
Barry, III

(10) Patent No.: US 9,443,276 B2
(45) Date of Patent: Sep. 13, 2016

(54) EVENT-BASED ASSET TRACKING, ORDER ADHERENCE, AND REWARDS MANAGEMENT WITH NFC-ENABLED ELECTRONIC DEVICES

(71) Applicant: Walter Richard Barry, III, Palo Alto, CA (US)

(72) Inventor: Walter Richard Barry, III, Palo Alto, CA (US)

( * ) Notice: Subject to any disclaimer, the term of this patent is extended or adjusted under 35 U.S.C. 154(b) by 554 days.

(21) Appl. No.: 13/844,534

(22) Filed: Mar. 15, 2013

(65) Prior Publication Data

US 2013/0222116 A1    Aug. 29, 2013

Related U.S. Application Data

(63) Continuation-in-part of application No. PCT/US2012/021794, filed on Jan. 19, 2012.

(60) Provisional application No. 61/624,351, filed on Apr. 15, 2012, provisional application No. 61/434,429, filed on Jan. 19, 2011, provisional application No. 61/442,160, filed on Feb. 11, 2011, provisional application No. 61/484,188, filed on May 9, 2011.

(51) Int. Cl.
| | |
|---|---|
| G06F 19/00 | (2011.01) |
| G06Q 10/08 | (2012.01) |
| G06Q 50/22 | (2012.01) |
| G06Q 20/32 | (2012.01) |
| H04W 4/00 | (2009.01) |

(52) U.S. Cl.
CPC ............ *G06Q 50/22* (2013.01); *G06F 19/327* (2013.01); *G06Q 10/087* (2013.01); *G06Q 10/0833* (2013.01); *G06Q 20/3278* (2013.01); *H04W 4/008* (2013.01)

(58) Field of Classification Search
None
See application file for complete search history.

(56) References Cited

U.S. PATENT DOCUMENTS

| 6,335,907 B1 | 1/2002 | Momich et al. |
| 7,002,476 B2 | 2/2006 | Rapchak |
| 7,639,120 B2 | 12/2009 | Sekura |

(Continued)

FOREIGN PATENT DOCUMENTS

| WO | 2008033954 A2 | 3/2008 |
| WO | 2012100009 A1 | 7/2012 |

OTHER PUBLICATIONS

International Searching Authority / US. International Search Report: International Patent Application No. PCT/US2012/021794, Mar. 26, 2012. 3 Pages.

(Continued)

*Primary Examiner* — Mohamed Barakat
(74) *Attorney, Agent, or Firm* — Dinsmore & Shohl LLP

(57) ABSTRACT

An electronic device enabled with a Near Field Communications ("NFC") reading capability may perform event-based asset tracking and/or order adherence, and/or rewards management in conjunction with a Software Service Platform. Assets may be provided with intelligent Radio Frequency Identification ("RFID") tags in which such is associated with a trackable event and such event may be associated with a master order of one or more such events. The electronic device may be programmable such that the various functions may be provided by application programs which may be preloaded on the electronic device as one or more client applications, provided to the NFC-enabled electronic device as a "software as a service" ("SaaS") delivery, or provided to the NFC-enabled electronic device in any other desired manner.

14 Claims, 20 Drawing Sheets

(56) References Cited

U.S. PATENT DOCUMENTS

| | | | |
|---|---|---|---|
| 7,762,457 B2 | 7/2010 | Bonalle et al. | |
| 2003/0130895 A1* | 7/2003 | Antonucci | B01J 23/6562 |
| | | | 705/14.27 |
| 2005/0277872 A1 | 12/2005 | Colby, Jr. et al. | |
| 2006/0113370 A1 | 6/2006 | Taylor et al. | |
| 2007/0219794 A1* | 9/2007 | Park | G06Q 10/10 |
| | | | 704/246 |
| 2007/0243934 A1* | 10/2007 | Little | G07F 17/32 |
| | | | 463/40 |
| 2007/0273517 A1 | 11/2007 | Govind | |
| 2008/0009344 A1* | 1/2008 | Graham | G07F 17/32 |
| | | | 463/25 |
| 2009/0021788 A1 | 1/2009 | Hoffman et al. | |
| 2010/0015584 A1* | 1/2010 | Singer | G06Q 30/02 |
| | | | 434/236 |
| 2010/0097195 A1* | 4/2010 | Majoros | G06K 7/0008 |
| | | | 340/10.6 |
| 2010/0155475 A1 | 6/2010 | Paek et al. | |
| 2010/0274591 A1 | 10/2010 | Wells | |
| 2010/0324936 A1* | 12/2010 | Vishnubhatla | G06F 19/322 |
| | | | 705/3 |

OTHER PUBLICATIONS

International Searching Authority / US. Written Opinion of the International Searching Authority: International Patent Application No. PCT/US2012/021794, Mar. 26, 2012. 7 Pages.

Barry, Walter R. Event-Based Medical Asset Tracking with NFC-Enabled Electronic Devices, U.S. Appl. No. 61/434,429, Jan. 19, 2011. 29 pages.

Barry, Walter R. Event-Based Medical Asset Tracking and Payment with NFC-Enabled Electronic Devices, U.S. Appl. No. 61/442,160, Feb. 11, 2011. 39 pages.

Barry, Walter R. Event-Based Medical Asset Tracking and Payment with NFC-Enabled Electronic Devices, U.S. Appl. No. 61/484,188, May 9, 2011. 71 pages.

Barry, Walter R. Event-Based Medical Asset Tracking and Rewards Management with NFC-Enabled Electronic Devices, U.S. Appl. No. 61/624,351, Apr. 15, 2012. 99 pages.

European Patent Office. Extended European Search Report: European Patent Application No. 12 736 667.2, Jun. 30, 2014. 6 Pages.

Kalayoglu, Murat V. et al. An Intermittent Reinforcement Platform to Increase Adherence to Medications. Am. J. Pharm. Benefits, vol. 1, No. 2, 2009. pp. 91-94.

IP Australia (Australian Patent Office). Patent Examination Report No. 1: Australian Patent Application No. 2012207300, Aug. 20, 2015. 2 Pages.

* cited by examiner

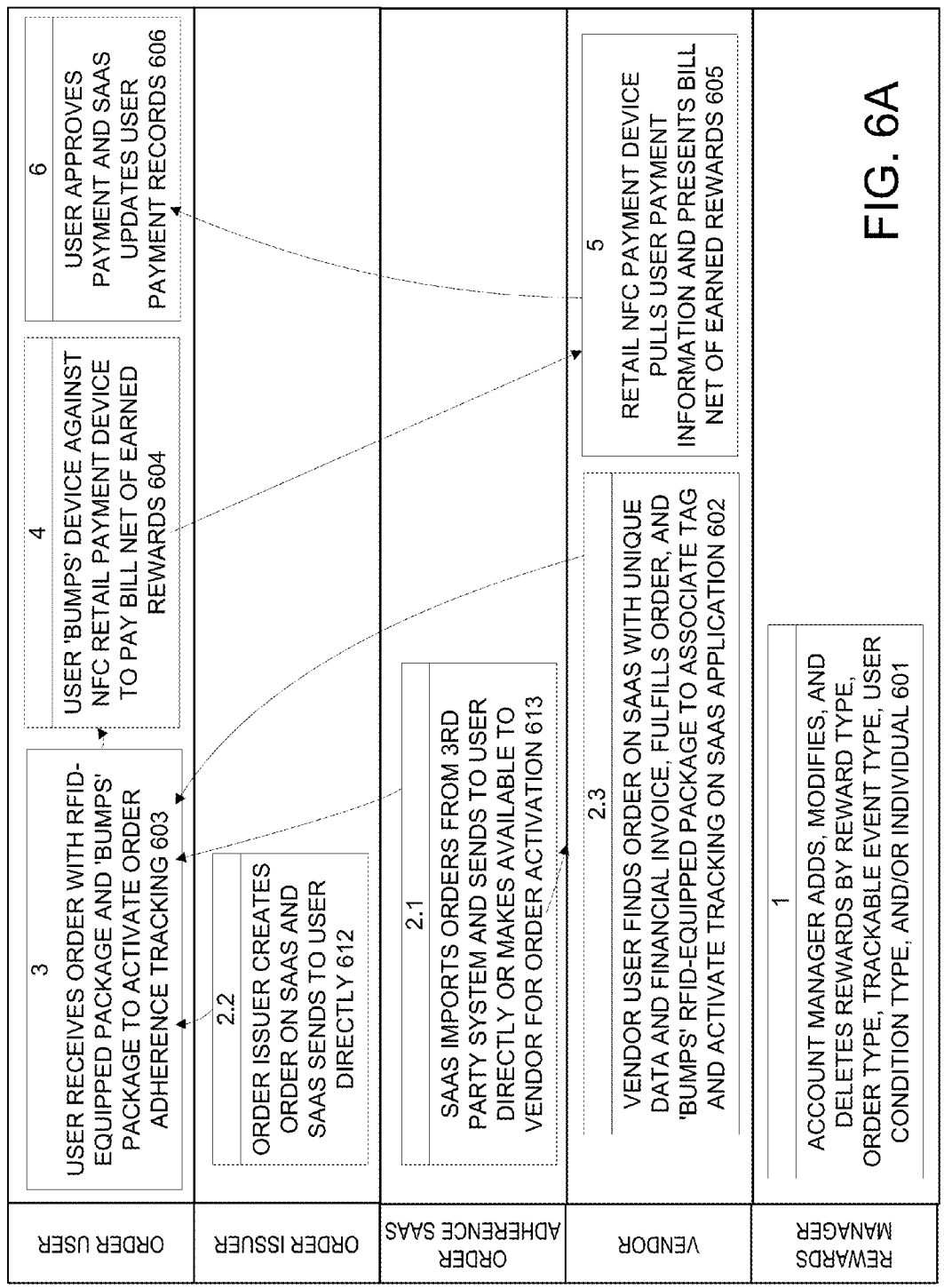

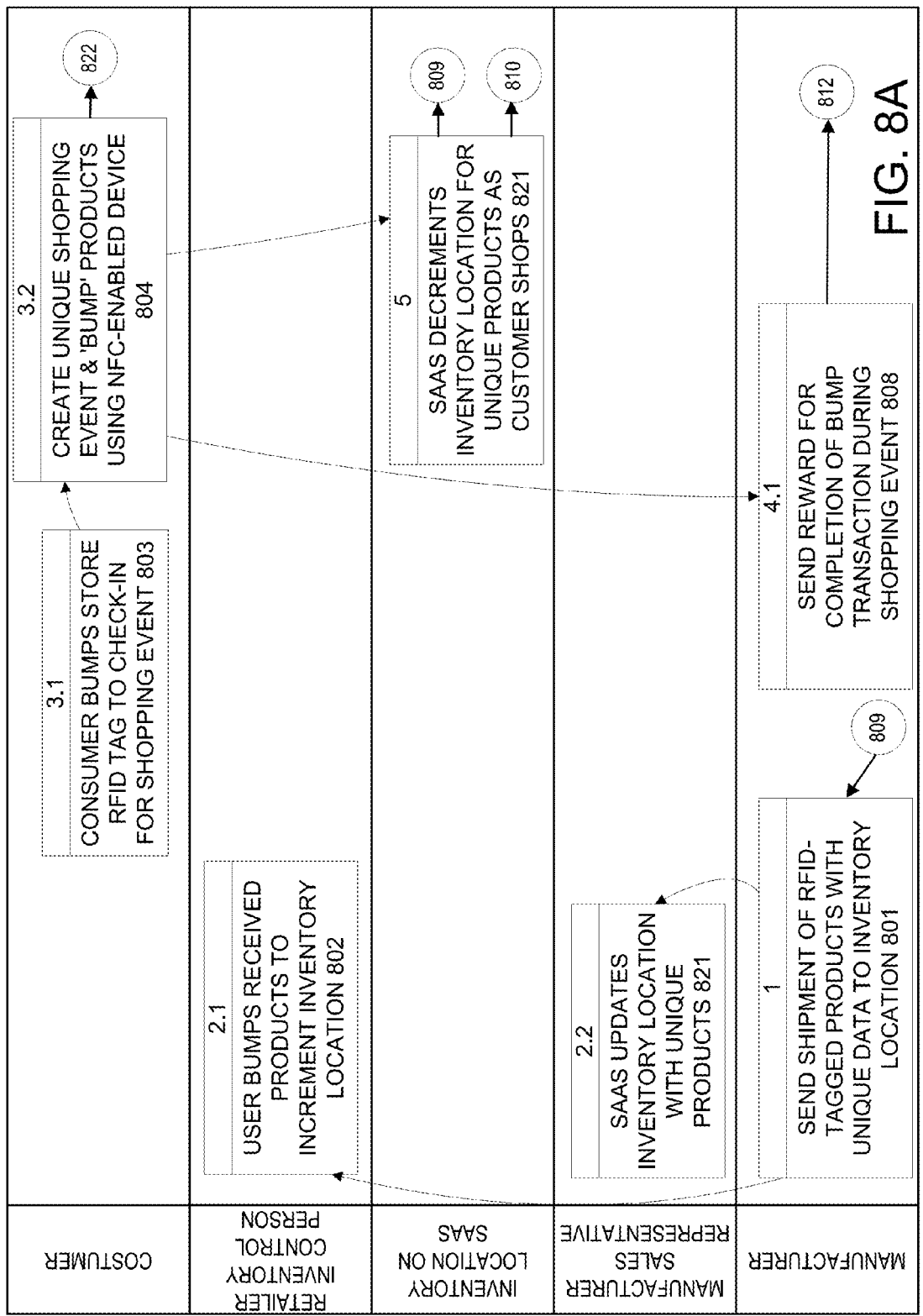

EVENT-BASED ASSET TRACKING, ORDER ADHERENCE, AND REWARDS MANAGEMENT WITH NFC-ENABLED ELECTRONIC DEVICES

CROSS-REFERENCE TO RELATED APPLICATIONS

This application claims the benefit of U.S. Provisional Patent Application Ser. No. 61/624,351 filed Apr. 15, 2012, which hereby is incorporated herein in its entirety by reference thereto. This application also is a continuation-in-part of International Patent Application No. PCT/US2012/021794 filed Jan. 19, 2012, which claims the benefit of U.S. Provisional Patent Application Ser. No. 61/434,429 filed Jan. 19, 2011, U.S. Provisional Patent Application Ser. No. 61/442,160 filed Feb. 11, 2011, and U.S. Provisional Patent Application Ser. No. 61/484,188 filed May 9, 2011, all of which hereby are incorporated herein in their entirety by reference thereto.

BACKGROUND OF THE INVENTION

1. Field of the Invention

The present invention relates to event-based asset tracking, order adherence, and rewards management for health care and other industries in which people or entities associate items (for example, supplies or services) with trackable events that may be associated with a master order program of one or more trackable events and which may include management of rewards associated with such trackable events.

2. Description of the Related Art

Current event-based field service or surgical asset tracking software applications rely upon use of a hand held bar-code scanner with a USB cable or BlueTooth connection to an internet-connected device. However, the bar code labels with its related content do not provide sufficient information for may stakeholders, so that the stakeholders in the event do not have the information they need in a timely manner to make informed decisions.

Current medication adherence technologies and related service providers have a limited physical authentication regime of the medication consumption event, and in particular, they have little assurance that the patient really consumed the medication. Moreover, medication adherence incentive programs rely on patient refill process as the measure of adherence, which is unreliable.

BRIEF SUMMARY OF THE INVENTION

One embodiment of the invention is an NFC-enabled electronic device comprising: a processor; a memory accessible to the processor; and a NFC reader under control of the processor; wherein the memory stores processor-executable instructions in one or more programs to perform n-Item asset tracking, the instructions comprising: instructions for identifying an occurrence of a Trackable Event based on proximity of the NFC reader to an RFID tag containing Unique Data; instructions for accessing the Unique Data and associating the Unique Data with the Trackable Event; instructions for maintaining and storing Trackable Event data including Unique Data in the device memory and through any database server; and instructions for reporting the Trackable Event data of RFID-equipped Items to an authorized Individual(s) including, but not limited to Item or Order activation, consumption, increment, transfer, or re-order transactions; compliance with a unique Order; or conformity with any regulations or laws.

Another embodiment of the invention is an NFC-enabled electronic device comprising: a processor; a memory accessible to the processor; and a NFC reading capability under control of the processor; wherein the memory stores processor-executable instructions in one or more programs to perform medical asset tracking, the instructions comprising: instructions for identifying an occurrence of a trackable event based on proximity of an RFID tag; instructions for accessing unique data on the RFID tag; instructions for maintaining trackable event data in accordance with the trackable event occurrence and the unique information; and instructions for reporting the trackable event data.

Another embodiment of the invention is the NFC-enabled electronic device as any of the preceding two paragraphs wherein: the trackable event is a trackable event of an Item; the unique data comprises Item, Individual, and/or Order data; and the asset tracking instructions further comprise: instructions for initially associating the RFID tag with the supply item; and instructions for wirelessly communicating the trackable event data and the Item, Individual, and/or Order data to a remote system. Yet another embodiment of the invention is the NFC-enabled electronic device as in any of the preceding two paragraphs wherein: the trackable event is consumption of an Order item by an individual; the unique data comprises adherence data; the trackable event data is consumption data; and the asset tracking instructions further comprise: instructions for wirelessly communicating the consumption data and the Order adherence data to a remote system.

Another embodiment of the invention is the NFC-enabled electronic device as in any of the preceding paragraphs wherein the program is a "Software as Service" ("SaaS") application.

Another embodiment of the invention is a Software as a Service Platform comprising: a database server; a web and application server; and a security architecture compliant with Health Insurance Portability and Accountability Act security requirements (if and as necessary for use), the Platform being programmed with platform-executable instructions comprising: instructions for receiving production schedules or orders from customers with Unique Data; instructions for managing RFID tag production associating a unique RFID tag with Unique Data for a unique Item; instructions for receiving an Order with Unique Data from an order fulfillment system such as a prescription order system and associates with a RFID-equipped Supply Package in a one-to-one relationship; instructions for embedding Unique Data on the RFID tag using an NFC-enabled device if necessary; instructions for managing a global asset registry of RFID tags associated with RFID-equipped Items each with Unique Data; instructions for authenticating use of RFID-equipped Item tag in a Trackable Event back to the RFID tag production origination date; and instructions for reporting the RFID (and associated Supply) life cycle to authorized entities.

Another embodiment of the invention is a Software as a Service System comprising: a Software as Service Platform comprising: a database server; a web and application server; and a security architecture compliant with Health Insurance Portability and Accountability Act security requirements; and an NFC-enabled electronic device comprising: a processor; a memory accessible to the processor; a NFC reader under control of the processor; and communications circuitry under control of the processor; wherein the memory stores processor-executable instructions in one or more programs, the processor-executable instructions comprising: instructions for wirelessly synchronizing with the Platform; instructions for identifying an occurrence of a Trackable Event based on proximity of the NFC reader to an RFID tag containing Unique Data; instructions for accessing the Unique Data and associating the Unique Data with the Trackable Event; instructions for maintaining and storing Trackable Event data including Unique Data in the device memory and through any database server; and instructions for reporting the Trackable Event data of RFID-equipped Items to an authorized person including, but not limited to Item or Order activation, consumption, increment, transfer, or re-order transactions; compliance with a unique Order; or conformity with any regulations or laws.

Another embodiment of the invention is the Software as a Service platform as in any of the preceding two paragraphs wherein the processor-executable instructions further comprise instructions for: maintaining, storing, and sharing payment information with third party NFC payment devices; calculating Individual's payment obligation based on Individual's eligibility of benefits from their insurance company; posting bill; and processing approved payment to a third party payment device.

Another embodiment of the invention is an asset tracking method comprising: identifying an occurrence of a Trackable Event based on proximity of the NFC reader to an RFID tag containing Unique Data; accessing the Unique Data and associating the Unique Data with the Trackable Event; maintaining and storing Trackable Event data including Unique Data in the device memory and through any database server; and reporting the Trackable Event data of RFID-equipped Items to an authorized person(s) including, but not limited to Item or Order activation, consumption, increment, transfer, or re-order transactions; compliance with a unique Order; or conformity with any regulations or laws.

Another embodiment of the invention is an asset tracking method comprising: receiving production schedules or orders from customers with Unique Data; managing RFID tag production associating a unique RFID tag with Unique Data for a unique Supply Item; receiving an Order with Unique Data from an order fulfillment system such as a prescription order system and associates with a RFID-equipped Supply Package in a one-to-one relationship; embedding Unique Data on the RFID tag using an NFC-enabled device if necessary; managing an asset registry of RFID tags associated with RFID-equipped Supply items each with Unique Data; authenticating use of RFID-equipped Supply item tag in a Trackable Event back to the RFID tag production origination date; and a program component for reporting the RFID (and associated Supply) life cycle to authorized entities.

Another embodiment of the invention is an asset tracking method comprising: wirelessly synchronizing with a Software as Service Platform comprising a database server; a web and application server; and a security architecture compliant with Health Insurance Portability and Accountability Act security requirements; identifying an occurrence of a Trackable Event based on proximity of an NFC-enabled electronic device to an RFID tag containing Unique Data; accessing the Unique Data and associating the Unique Data with the Trackable Event; maintaining and storing Trackable Event data including Unique Data in a memory of the NFC-enabled electronic device and through any database server; and reporting the Trackable Event data of RFID-equipped Items to an authorized person including, but not limited to Item or Order activation, consumption, increment, transfer, or re-order transactions; compliance with a unique Order; or conformity with any regulations or laws.

Another embodiment of the invention is an asset tracking method comprising: identifying an occurrence of a trackable event based on proximity of an RFID tag; accessing unique data on the RFID tag; and an application component for maintaining trackable event data in accordance with the trackable event occurrence and the unique information; and reporting the trackable event data.

Another embodiment of the invention is the asset tracking method of the preceding paragraph wherein: the trackable event is a trackable event of an Item; the unique data comprises Item/Supply, Individual, and/or Order data; the method further comprises: initially associating the RFID tag with the supply item; and wirelessly communicating the trackable event data and the Supply, Individual, and/or Order data to a remote system. Yet another embodiment of the invention is the asset tracking method of the preceding paragraph wherein: the trackable event is consumption of an Order-defined item by an individual; the unique data comprises adherence data; and the trackable event data is consumption data; the method further comprising wirelessly communicating the consumption data and the adherence data to a remote system.

Another embodiment of the invention is the asset tracking method of any of the five preceding paragraphs further comprising: maintaining, storing, and sharing payment information with third party NFC payment devices; calculating Individual's payment obligation based on Individual's eligibility of benefits from their insurance company; posting bill; and processing approved payment to a third party payment device.

Another embodiment of the invention is a non-transitory computer-readable medium storing computer-executable instructions in one or more computer programs, the computer-executable instructions comprising: instructions for receiving production schedules or orders from customers with Unique Data; instructions for managing RFID tag production associating a unique RFID tag with Unique Data for a unique Supply Item; instructions for receiving an Order with Unique Data from an order fulfillment system such as a prescription order system and associates with a RFID-equipped Supply Package in a one-to-one relationship; instructions for embedding Unique Data on the RFID tag using an NFC-enabled device if necessary; instructions for managing an asset registry of RFID tags associated with RFID-equipped Supply items each with Unique Data; instructions for authenticating use of RFID-equipped Supply item tag in a Trackable Event back to the RFID tag production origination date; and instructions for reporting the RFID (and associated Supply) life cycle to authorized entities.

Another embodiment of the invention is a non-transitory computer-readable medium storing computer-executable instructions in one or more computer programs, the computer-executable instructions comprising: instructions for wirelessly synchronizing with a Software as Service Platform comprising a database server, a web and application server, and a security architecture compliant with Health Insurance Portability and Accountability Act security requirements; instructions for identifying an occurrence of a Trackable Event based on proximity of an NFC-enabled electronic device to an RFID tag containing Unique Data; instructions for accessing the Unique Data and associating the Unique Data with the Trackable Event; instructions for maintaining and storing Trackable Event data including Unique Data in a memory of the NFC-enabled electronic device and through any database server; and instructions for reporting the Trackable Event data of RFID-equipped Items to an authorized person including, but not limited to Supply or Medication activation, consumption, increment, transfer, or re-order transactions, or compliance with a unique Order, or conformity with any regulations or laws, or any combination thereof.

Another embodiment of the invention is a non-transitory computer-readable medium storing computer-executable instructions in one or more computer programs, the computer-executable instructions comprising: instructions for identifying an occurrence of a trackable event based on proximity of an RFID tag; instructions for accessing unique data on the RFID tag; instructions for maintaining trackable event data in accordance with the trackable event occurrence and the unique information; and instructions for reporting the trackable event data.

Another embodiment of the invention is the computer-readable medium of the preceding paragraph wherein: the trackable event is a trackable event of a supply item; the unique data comprises Supply, Individual, and/or Order data; and the computer-executable instructions further comprise: instructions for initially associating the RFID tag with the supply item; and instructions for wirelessly communicating the trackable event data and the Supply, Individual, and/or Order data to a remote system. Yet another embodiment of the invention is the computer-readable medium of the preceding paragraph wherein: the trackable event is consumption of an Order-defined item by an individual; the unique data comprises adherence data; the trackable event data is consumption data; and the processor-executable instructions further comprise instructions for wirelessly communicating the consumption data and the adherence data to a remote system.

Another embodiment of the invention is the computer-readable medium of any of the preceding four paragraphs wherein the computer-executable instructions further comprise: instructions for maintaining, storing, and sharing payment information with third party NFC payment devices; instructions for calculating Individual's payment obligation based on Individual's eligibility of benefits from their insurance company; instructions for posting bill; and instructions for processing approved payment to a third party payment device.

Another embodiment of the invention is the invention of any of the preceding eighteen paragraphs further comprising rewards management.

Another embodiment of the invention is a method of furnishing stakeholders with information about a plurality of trackable events having one or more items each equipped with one or more RFID tags associated therewith, comprising: providing a client software application for installation to a NFC-enabled device to acquire unique data corresponding to the trackable events, the trackable events being evidenced by a bump action between the NFC-enabled device and the one or more RFID tags at specific geo-locations, and the unique data including an individual's name and/or identification number, an event name and/or identification number, an item name, and a unique RFID code from the RFID tags, and date, time and geo-location data coincident with the trackable event as determined by the NFC-enabled device; receiving the unique data over a network from the NFC-enabled device; preparing from the unique data different forms of reporting content for a plurality of different groups of entities and roles by entity having different uses for the content; and furnishing the different forms of reporting content respectively to the entities and roles by entity. In a variation, the method further comprises: determining completion by the individual user of the trackable events; calculating an earned reward based on the individual user completion of the trackable events; and furnishing the earned reward to the NFC-enabled device. In yet another variation wherein the earned reward has a value, the method further comprises administering deduction of the value of the earned reward against an obligation; and reporting the deduction to the individual user.

Another embodiment of the invention is a software service platform comprising: a processor; a memory coupled to the processor, the memory storing processor-executable instructions in one or more programs to perform a method of furnishing stakeholders with information about a plurality of trackable events having one or more items each equipped with one or more RFID tags associated therewith, the instructions comprising: instructions for providing a client software application for installation to a NFC-enabled device to acquire unique data corresponding to the trackable events, the trackable events being evidenced by a bump action between the NFC-enabled device and the one or more RFID tags at specific geo-locations, and the unique data including an individual's name and/or identification number, an event name and/or identification number, an item name, and a unique RFID code from the RFID tags, and date, time and geo-location data coincident with the trackable event as determined by the NFC-enabled device; instructions for receiving the unique data over a network from the NFC-enabled device; instructions for preparing from the unique data different forms of reporting content for a plurality of different groups of entities and roles by entity having different uses for the content; and instructions for furnishing the different forms of reporting content respectively to the entities and roles by entity.

BRIEF DESCRIPTION OF THE SEVERAL VIEWS OF THE DRAWINGS

FIGS. 6A and 6B are sections of a schematic diagram of rewards management using an NFC-enabled device.

FIGS. 8A and 8B are sections of a schematic diagram of consumer retail shopping using an NFC-enabled device.

DETAILED DESCRIPTION OF THE INVENTION, INCLUDING THE BEST MODE

Figure 4A:
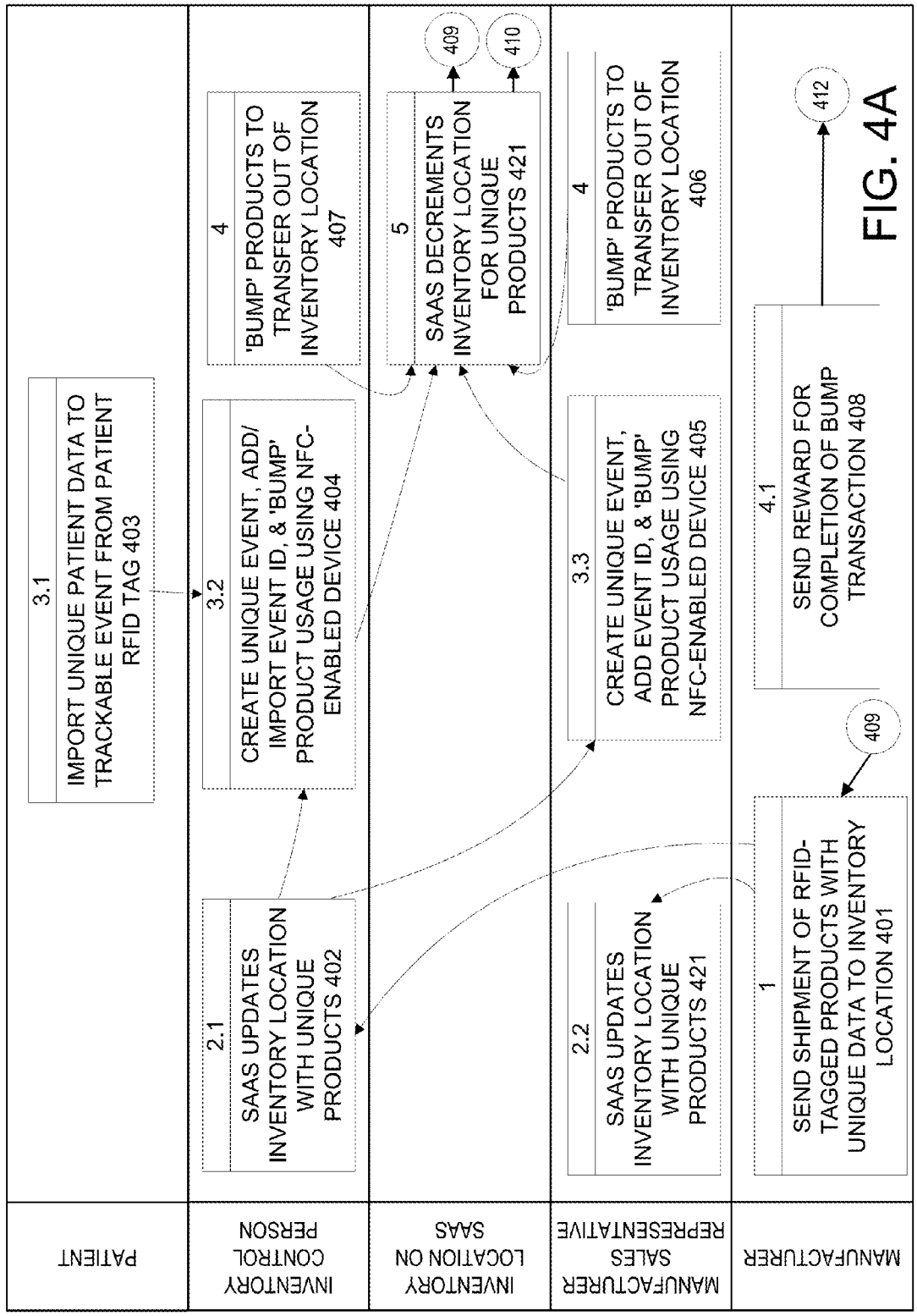
FIGS. 4A and 4B are sections of a schematic diagram of event-based asset tracking using an NFC-enabled device.
Figure 4B:
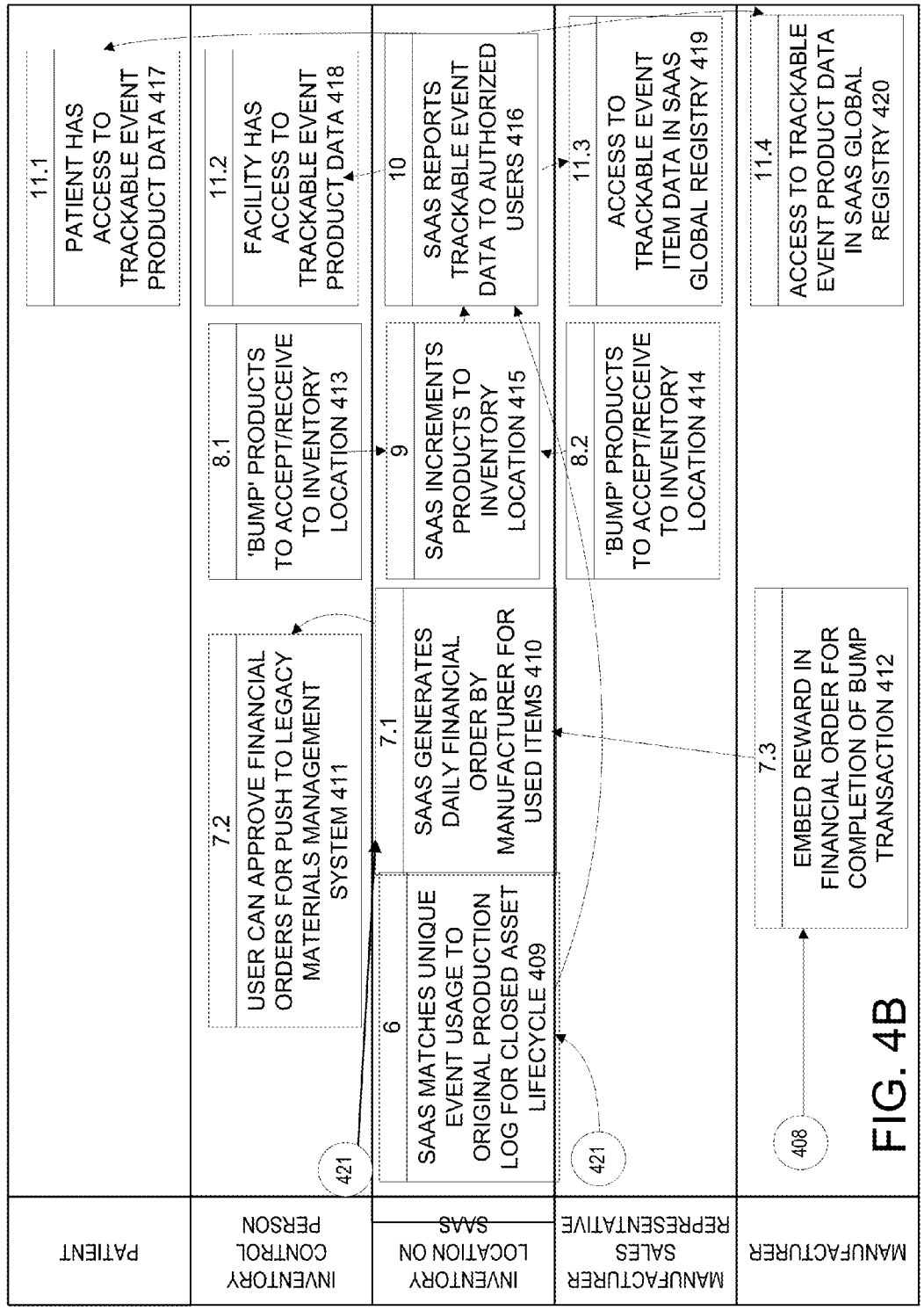
Figure 5A:
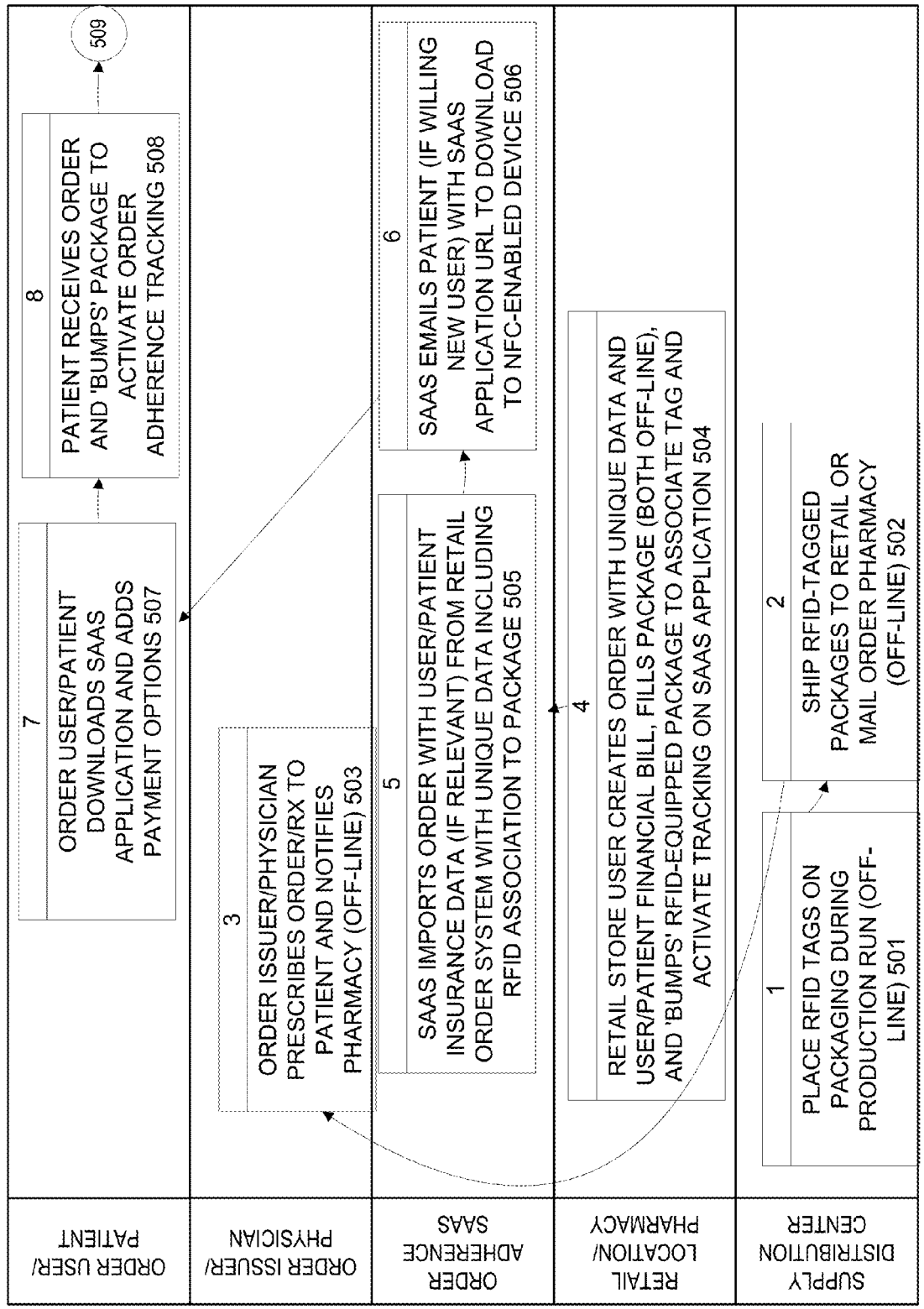
FIGS. 5A and 5B are sections of a schematic diagram of order adherence tracking using an NFC-enabled device.
Figure 5B:
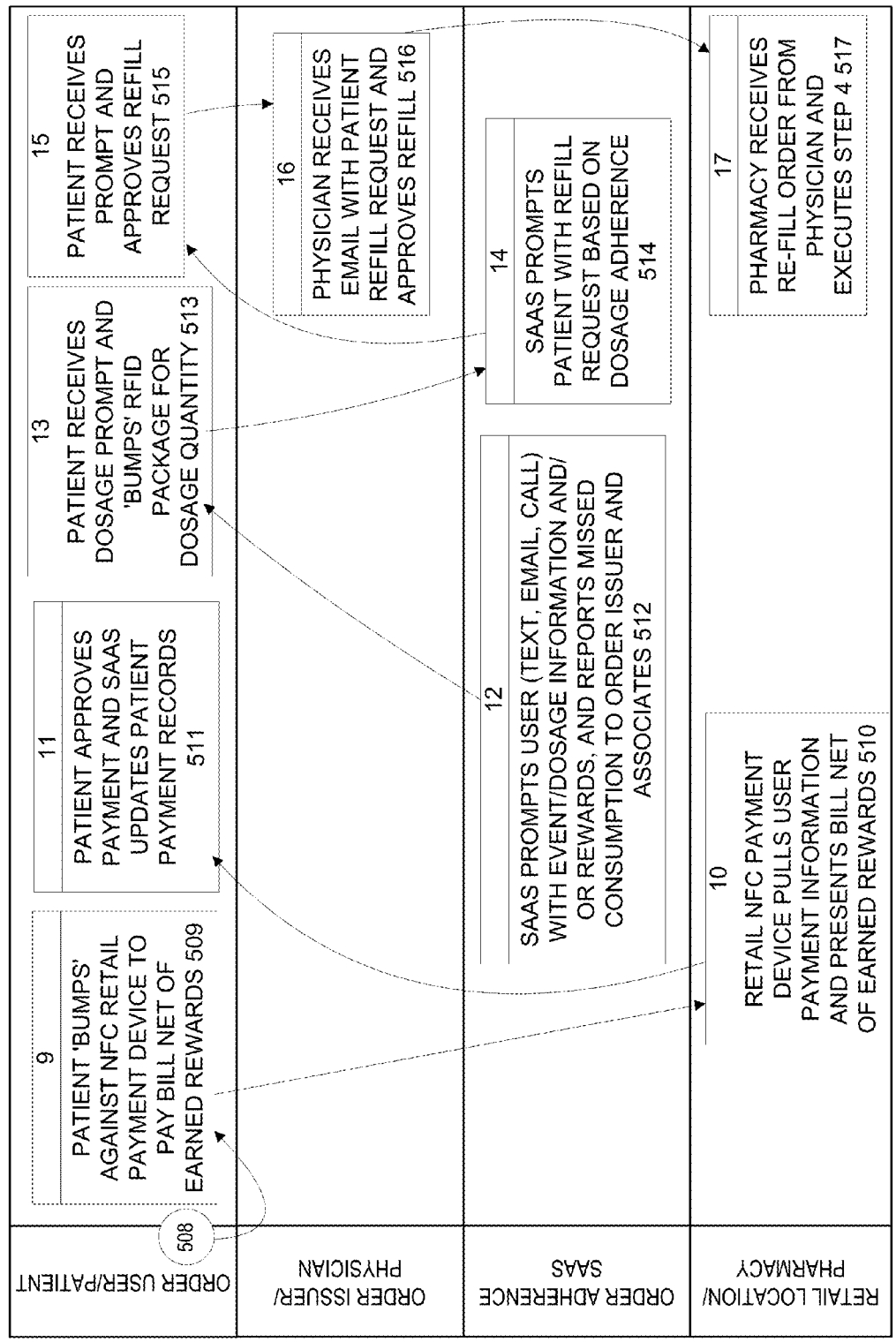
Figure 6B:
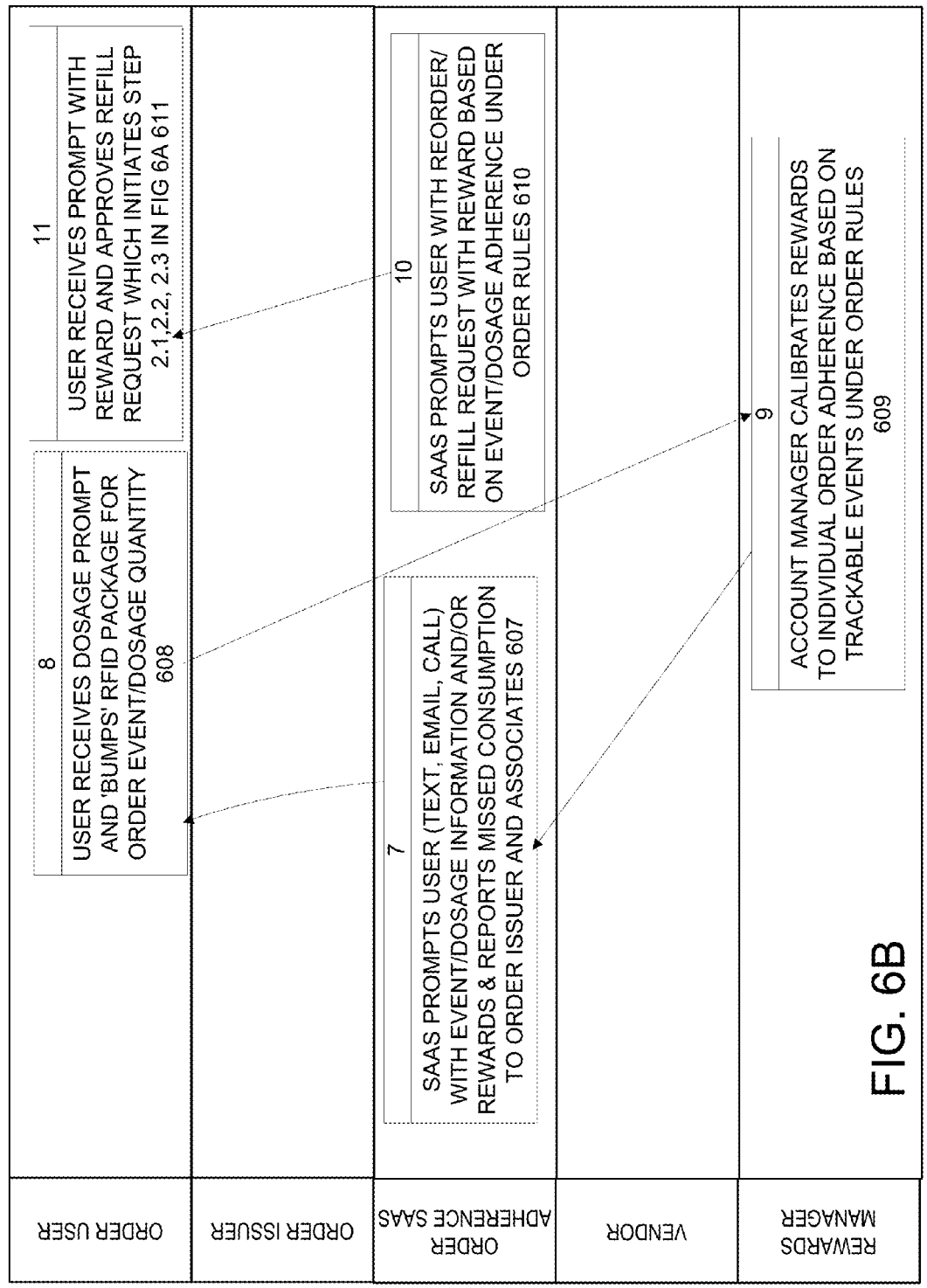

An electronic device 100 (FIG. 1) enabled with a Near Field Communications ("NFC") reading capability may perform event-based asset tracking as shown in FIGS. 4A and 4B, and/or order adherence as shown in FIGS. 5A and 5B, and/or rewards management as shown in FIGS. 6A and 6B. Assets may be provided with intelligent Radio Frequency Identification ("RFID") tags 103, in which such is associated with trackable event and such event may be associated with a master order of one or more such events. The electronic device 100 may be programmable such that the various functions may be provided by application programs which may be preloaded on the electronic device 100 as one or more client applications 105, provided to the NFC-enabled electronic device as a "software as a service" ("SaaS") delivery 203, or provided to the NFC-enabled electronic device in any other desired manner.

Suitable electronic devices which may be NFC-enabled when manufactured, or later modified by the use of add-on or plug-in units, or in any other manner include, for example, mobile digital devices, personal digital assistants, smart phones, tablet computers, netbooks and personal computers.

The term "Trackable Events" refers to events in which one or more individuals ("Individual or User") are associated with a date, time, geographic location, and one or more items such as, for example, products or services ("Items or Supplies") that may or may not be associated with a master order ("Order") and that may or may not be ordered for Individual by another person or entity ("Order Issuer"). By way of health care example, a Trackable Event may include, but not be limited to, a surgery, medication dosage event, and inventory addition or transfer.

Items may be any supply or service that can hold a radio frequency identification ("RFID") tag, such as, for example, medical supplies, devices, instruments, equipment, pharmaceutical prescription supplies, over-the-counter supplies, or nutritional supplies.

Order may include, by way of example, a prescription order with a series of dependent dosage events (for example, trackable events) based on a pre-established date, time, item, and item dosage volume, and dosage schedule by an Order Issuer.

Order Issuer may include, by way of example, a physician.

The term "Unique Data" refers to uniquely identifiable Item(s), Individual(s), and/or Order data which may be embedded on the RFID tag around uniquely identifiable and authenticated Trackable Events.

A variety of different types of RFID tags are available. The passive high frequency ("HF") RFID tags and Near Field Communication ("NFC") technologies are particular suitable for the various applications described herein.

The term "Rewards" refers to any type of incentive or reward provided to one or more Individuals by a person or entity to complete one or a series of Trackable Events that achieve a pre-defined performance target established by the Person or Entity providing the Rewards. An illustrative example of a suitable type of Rewards and behavior modification could be an intermittent reward as described in further detail in US Patent Application Publication No. 2010/0015584 published Jan. 21, 2010 in the name of Michael S. Singer et al., which is incorporated herein in its entirety by reference thereto and appended hereto. Many other types of incentives as well as various schedules, business rules, payment options, and so forth may also be suitable. Intelligent, uniquely identifiable Item and Individual data may be added to the RFID tag for use by the application.

In an illustrative implementation, for example, the SaaS and/or RFID tag 103 holds Unique Data to inform the NFC-enabled electronic device to effectively authenticate, manage, and report Individual Item consumption and apply rewards to authorized users such as the Individual and care providers.

RFID Tags

The International Organization for Standards ("ISO") has defined frequency standards in the Low Frequency (LF), High Frequency (HF), Ultra-High Frequency (UHF) and microwave or Super-High Frequency (SHF) bands. As a rule of thumb, the higher the frequency is, the more data can be transmitted, the longer maximum read-out distances are and, as a consequence, the more functionality can be added to the tag. For LF tags, the technical read-out distance is a few centimeters, for HF and UHF tags a few meters and for tags operating in the microwave band up to hundreds of meters. For supply chain purposes, the two frequency bands (860-960 MHz and 433 MHz) in the UHF spectrum are particularly useful.

There are three types of RFID tags: passive RFID tags which have no power source and require an external electromagnetic field to initiate a signal transmission, active RFID tags which contain a battery and can transmit signals once an external source ('Interrogator') has been successfully identified, and battery assisted passive (BAP) RFID tags which require an external source to wake up but have significant higher forward link capability providing greater range. RFID tags may provide a small memory ("RFID Memory"), which size depends on the RFID chipset technology. Active RFID tags include sensors that can carry and broadcast out to other receiving/reader devices.

Near Field Communication ("NFC") is a short-range high frequency wireless communication technology, which enables the exchange of data between devices or a device and a high frequency RFID tag over about a 10 centimeter (around 4 inches) distance.

Storage of Unique Data on RFID Tag

Figure 1:
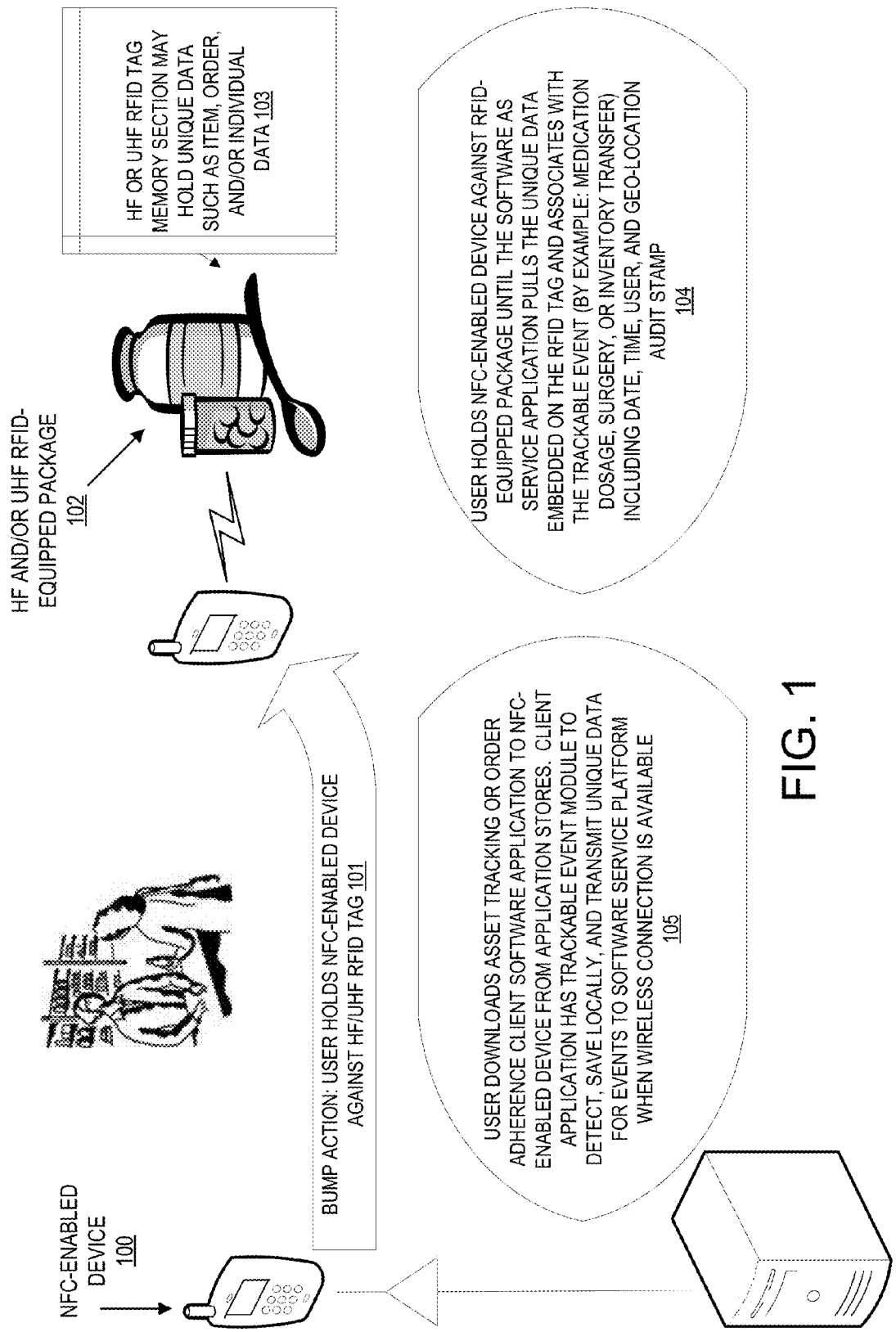
FIG. 1 is a schematic diagram of a bump transaction.

FIG. 1 shows a NFC-enabled electronic device which includes NFC reading circuitry for reading data embedded in the memory and sensory chip set of a HF or UHF RFID tag 103 within a very short distance. The passive HF and/or UHF RFID tag 103 may be applied to a package 102 and may hold uniquely identifiable Item data including, but not limited to, catalog code, lot code, expiration date, and item description. As RFID memory capacity permits, additional Unique Data may be added. Unique Data may include, but not be limited to, Supply data (manufacturer name and industry classification identifier code (such as, for example, GS1, HIBC for health care), product catalog code, item description, unit of measure quantity, unit of measure type, lot or serial code, and expiration data); Individual data (individual name, insurance company name, insurance identification number, individual record number, date of birth, address, and mobile/text and email information); and Order data (order number, item name, item catalog code number, lot/serial number, consumption quantity, total quantity, Event (for example, dosage) schedule, Order (for example, a prescription) expiration date, refill orders, item (for example, medication) side-effects and responses, 'do not mix' list, Order Issuer (for example, the prescribing physician), retail location name, address, and contact information, and so forth.

The BUMP Transaction

FIG. 1 shows an illustrative bump transaction with an NFC-enabled device 100. A Trackable Event Detection module 105 which may be running on the device in background or opened by the user as needed detects the RFID tag 103 and pulls the Unique Data embedded on the RFID tag 103 when the device is held near or against the RFID-equipped package 102, thereby detecting a Trackable Event 101. In one illustrative implementation, a user moves either the NFC-enabled device 100 or the Item or package 102 marked with the RFID tag 103 or both to within ten centimeters of one another. The user may touch (bumps or taps) the NFC-enabled device 100 or the Item or package 102 marked with the RFID tag 103 to one another, or may hold the two against one another. Where the RFID tag is a passive tag, it is activated by a power signal emitted by the NFC-enabled device.

While the bump transaction is a convenient and effective way to detect a Trackable Event, other techniques may be used instead, if desired. In an alternative technique that need not be triggered by proximity, the user touches a button (physical or virtual) on the NFC-enabled device to acknowledge the Trackable Event, at which time the appropriate RFID tag (corresponding, for example, to the particular button touched if multiple choices are presented) is detected and its unique RFID number along with the Unique Data is read. A requirement for entry of a security code may be included if desired. In this alternative, use of a type of RFID tag having a greater range may be desirable such as UHF RFID tag. In another alternative technique, a screen or voice prompt notifies the user of the Trackable Event and the user responds orally by speaking into the NFC-enabled device to acknowledge the Trackable Event. Any type of oral response may be required, ranging from a simple yes/no acknowledgement to confirming the Trackable Event by name. A requirement for a spoken security code may be included if desired. At that time the appropriate RFID tag is detected and its unique RFID number along with the Unique Data is read. In this alternative, use of a type of RFID tag having a greater range may be desirable.

The processes shown in FIG. 1 include the following: bump action wherein user holds NFC-enabled device against HF/UHF RFID tag (block 101), HF or UHF RFID tag memory section may hold Unique Data such as Item, Order, and/or Individual data (block 103), user holds NFC-enabled device against RFID-equipped package until the Software as Service application pulls the Unique Data embedded on the RFID tag and associates with the Trackable Event (by example: medication dosage, surgery, or inventory transfer) including date, time, user, and geo-location audit stamp (block 104) and user downloads Asset Tracking or Order Adherence client software application to NFC-enabled device from application stores. Client application has Trackable Event module to detect, save locally, and transmit Unique Data for Events to Software Service platform when wireless connection is available (block 105).

FIG. 2 shows how a bump transaction may be used for rewards management and payment. In order to complete payment transactions, for example, a third party user may present a user a NFC payment device and "bump" against the User's NFC-enabled device. The payment transaction, net of any earned Rewards associated with Completed Trackable Events, may be completed using cloud computing resources, as described elsewhere in this document.

Figure 2A:
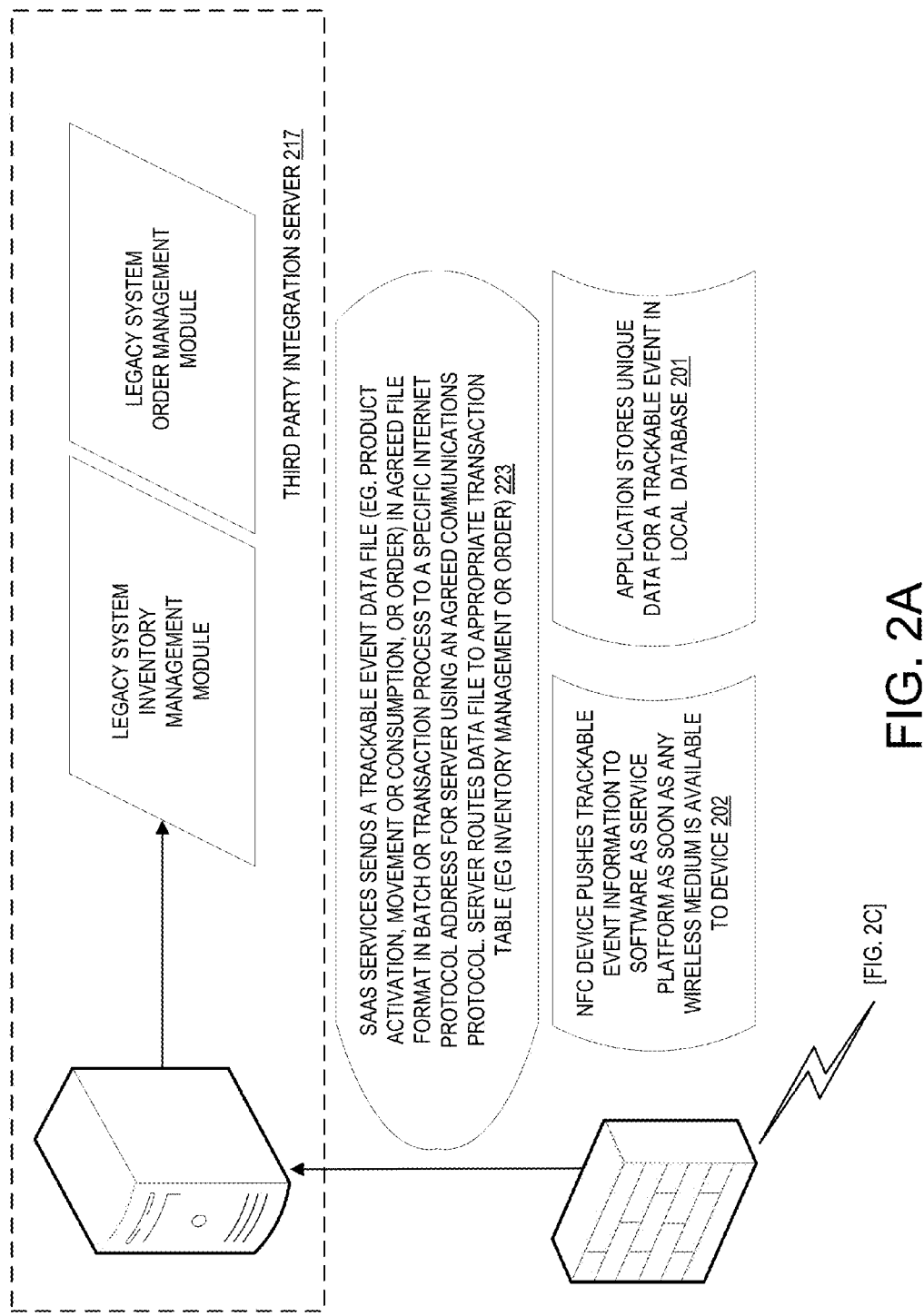
FIGS. 2A, 2B, 2C and 2D are sections of a schematic diagram of a Trackable Event data collection, storage, reporting, rewards management, and payment services on a "Software as a Service" platform using an NFC-enabled device.

The processes shown in FIG. 2A include the following: application stores Unique Data for a Trackable Event in local database (block 201), NFC device pushes Trackable Event information to Software as Service platform as soon as any wireless medium is available to device (block 202), and SaaS Services sends a trackable event data file (for example, Product activation, movement or consumption, or order) in agreed file format in batch or transaction process to a specific internet protocol address for server using an agreed communications protocol. Server routes data file to appropriate transaction table (for example, inventory management or order) (block 223).

Figure 2B:
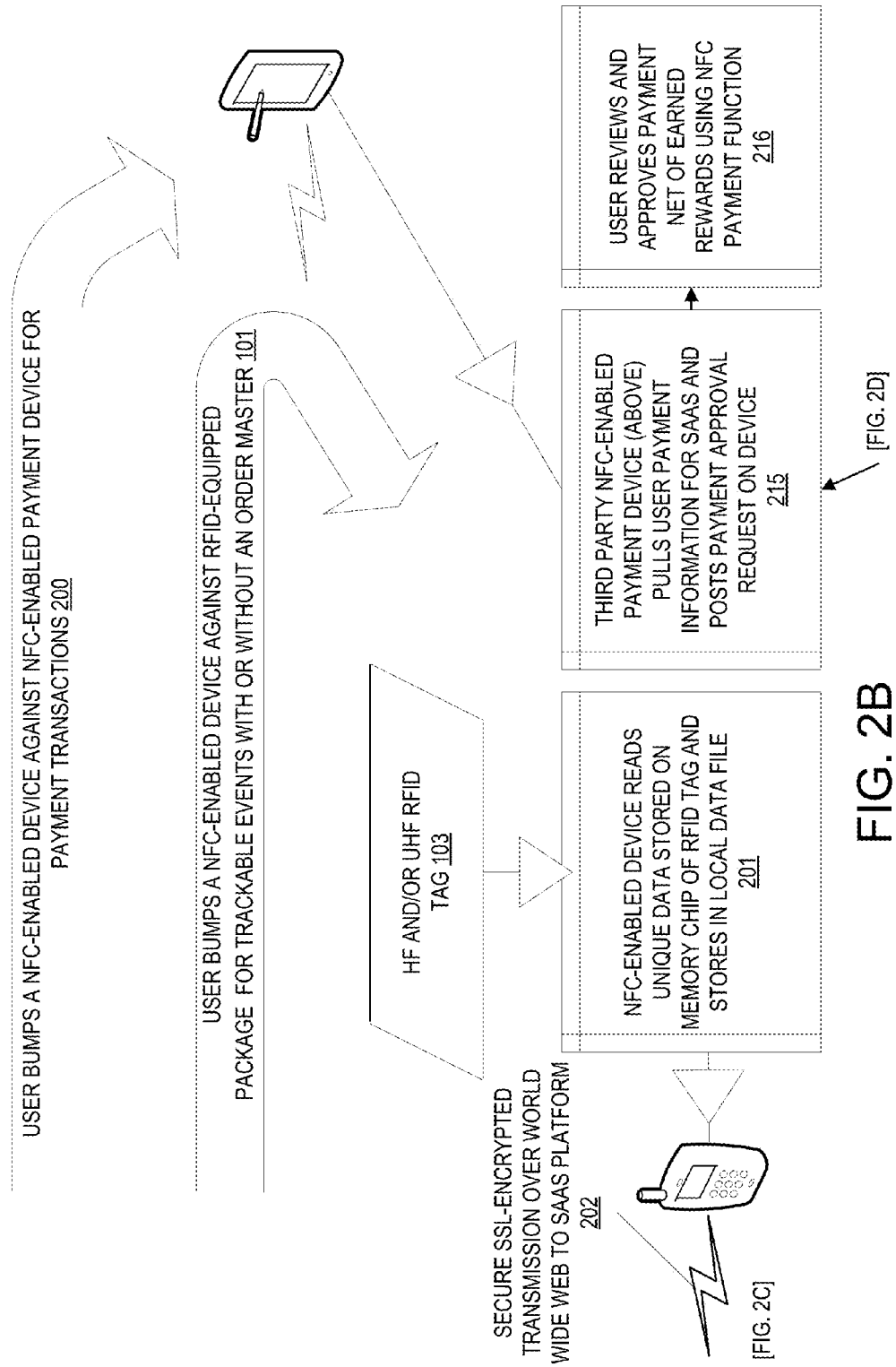

The processes shown in FIG. 2B include the following: user bumps a NFC-enabled device against RFID-equipped package for Trackable Events with or without an Order master (block 101); User bumps a NFC-enabled device against NFC-enabled payment device for payment transactions (block 200); NFC-enabled device reads Unique Data stored on memory chip of RFID tag and stores in local data file (block 201); secure SSL-encrypted transmission over world wide web to SaaS Platform (block 202); third party NFC-enabled payment device (above) pulls user payment information for SaaS and posts payment approval request on device (block 215); user reviews and approves payment net of earned Rewards using NFC payment function (block 216).

Figure 2C:
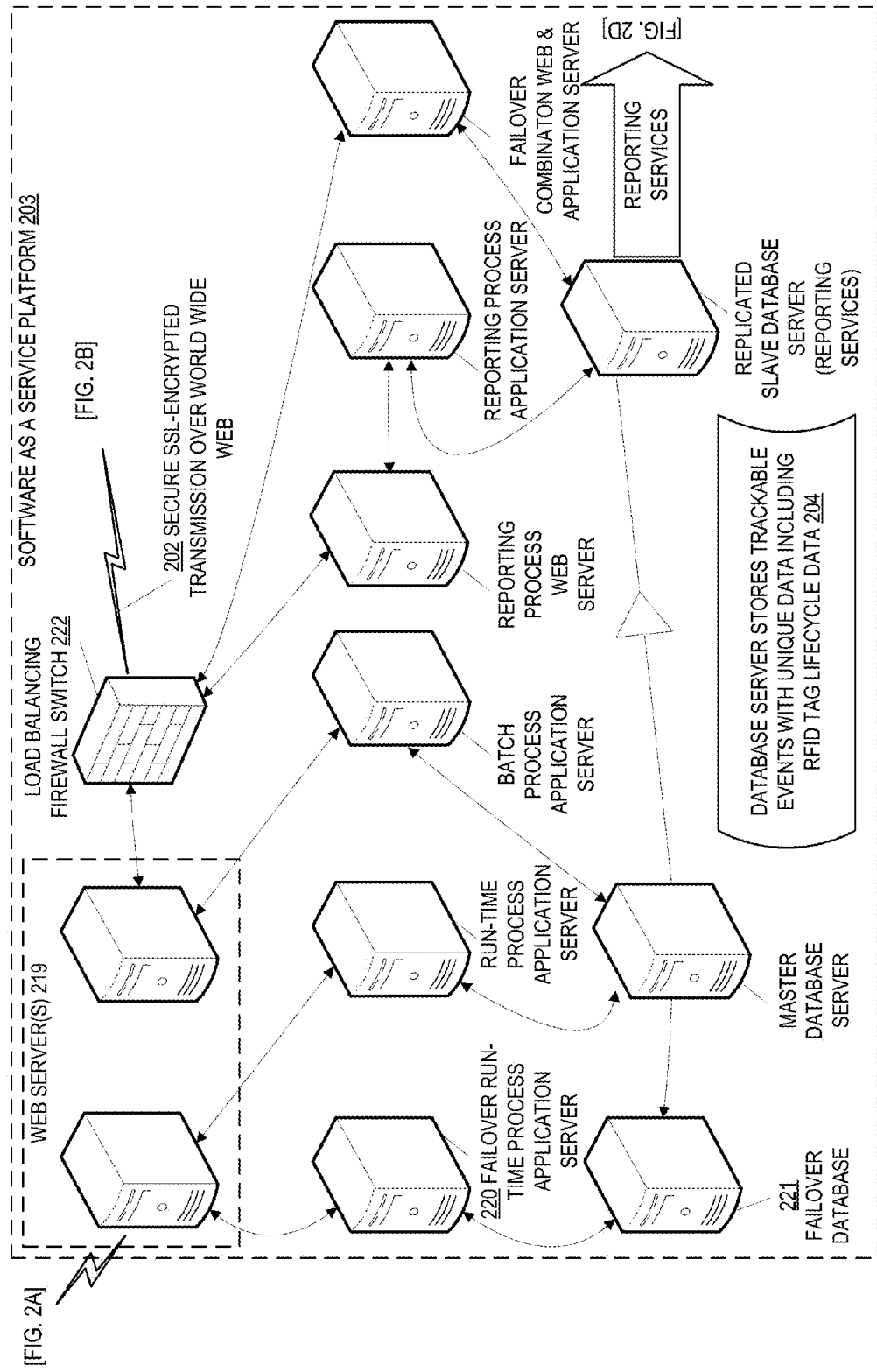

The processes shown in FIG. 2C include the following: secure SSL-encrypted transmission over world wide web (block 202); database server stores Trackable Events with Unique Data including RFID lifecycle data (block 204).

Figure 2D:
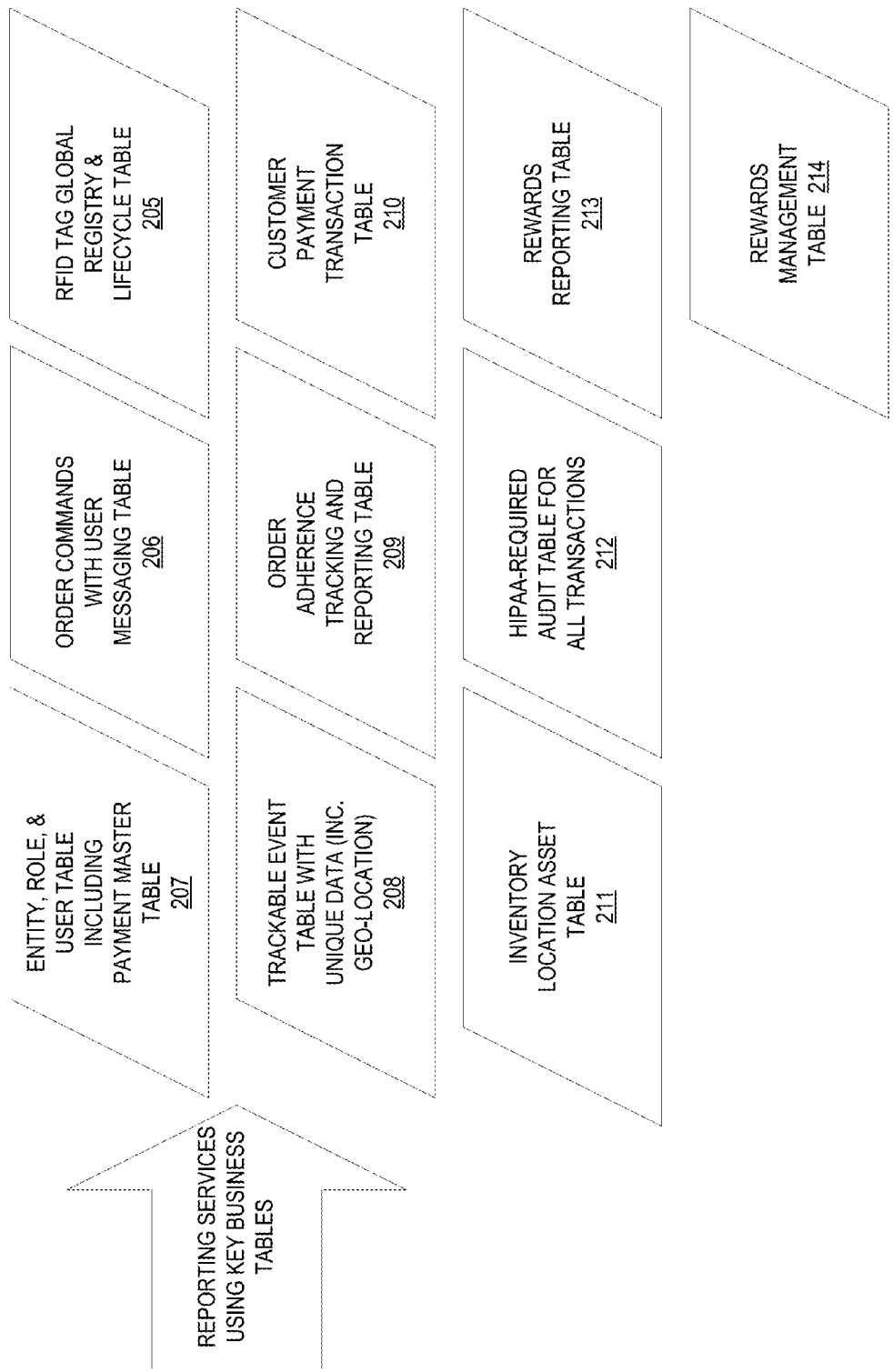

The following key business tables are shown in FIG. 2D: RFID tag global registry & lifecycle table 205, Order commands with User messaging table 206, Entity, Role, & User table including payment master table 207, Trackable Event table with Unique Data (including geo-location) 208, Order adherence tracking and reporting table 209, Customer payment transaction table 210, Inventory Location asset table 211, HIPAA-required audit table for ALL transactions 212, Rewards reporting table 213, and Rewards management table 214.

Software as Service Applications

Trackable Event detection with an NFC-enable device may be advantageously used in connection with cloud computing techniques, including, for example, a Software as a Service ("SaaS") platform, an example 203 of which is shown in FIGS. 2A, 2B, 2C and 2D. The Trackable Event application 105 running on the NFC-enabled device may operate in close cooperation with the SaaS platform 203. The user may initiate a Trackable Event on the SaaS application by "bumping" the NFC-enabled electronic device against an Item 101 so that the SaaS application may retrieve and post the unique RFID number and the Unique Data embedded on the RFID memory 103, and the SaaS application or other SaaS applications may complete the Trackable Event in any desired manner.

Trackable event detection with an NFC-enable device may also be advantageously used in connection with, for example, an Order Adherence Service provided on the SaaS platform, as shown in FIGS. 5A and 5B. In an illustrative example of Order Adherence Service, for example, a user opens the Trackable Event Application on the NFC-enabled device so that a trackable event may be detected. In this illustrative approach, the Order Adherence Service prompts to the user to initiate a trackable event (for example, medication dosage) with or without an associated Reward 512, and/or remains in a standby mode to recognize a bump transaction or other detection of a trackable event. Upon detection of a Trackable Event, the Trackable Event Application transmits the unique RFID number and the Unique Data 202 to another one or more SaaS applications 203 or third party customer applications for other desired action 217. Illustratively, one or more SaaS application or applications may associate the Unique Data with a unique system-generated Event Identification Number 208, and may verify and validate the Unique Data through the SaaS platform back to the original RFID production date for a complete asset life cycle reconciliation 205. In other words, the SaaS system may acknowledge the completion of a Trackable Event for a unique Item with a unique individual or event (blocks 208 and 421), and also associate the unique item back to the original product activation date on the SaaS database registry user, date, time, and geo-location stamp (table 205) from the manufacturer or retail location in order to authenticate the item's pedigree (table 205). The Activation date is the date when the Item is activated in the SaaS database registry with a date and time stamp (table 205). Every time a user bumps an Item 101 for either the Item Asset Tracking (FIGS. 4A and 4B) or Order Adherence Service (FIGS. 5A and 5B), for example, the SaaS platform may perform this 1:1 Item to Trackable Event association (table 208), and 1:1 match to the original production date.

Payment transactions with an NFC-enabled device may also be carried out in connection with cloud computing techniques such as an SaaS platform (blocks 200 and 215). As one example of a payment transaction, a third party user (for example, at a Retail location) may present a NFC payment device and "bump" it against the User's NFC-enabled device to generate an invoice. The SaaS Service may push the User's required information including payment information as well as apply any eligibility of rewards or benefits information (table 207), to enable accurate final bill presentment on the User's NFC-enabled device (block 215). The User may then review the transaction and indicate payment approval on the NFC-enabled device to the third party device to complete payment. The client application on the NFC-enabled device updates the SaaS platform with the payment transaction information for SaaS reporting purposes including any applied Rewards (block 216).

The SaaS platform 203 is a type of cloud computing. Cloud computing is location independent computing, whereby shared servers provide resources, software, and data to computers and other devices on demand, as with the electricity grid. Details are abstracted from consumers, who no longer have need for expertise in, or control over, the technology infrastructure "in the cloud" that supports them. Cloud computing describes a new supplement, consumption, and delivery model for IT services based on the Internet, and it typically involves over-the-Internet provision of dynamically scalable and often virtualized resources. This may take the form of web-based tools or applications that users can access and use through a web browser as if it were a program installed locally on their own computer.

The SaaS platform described herein, including the SaaS applications, enables users to identify, authenticate, and track Item consumption for Trackable Events associated to Individuals on NFC-enabled devices (table 208). The SaaS platform also enables individuals to share personal payment information between an appropriate SaaS application and a third party NFC payment device (table 207), receive a bill from such third party device (block 215), approve payment on the NFC-enabled device, and track payment history on the SaaS application (table 210). Supplies are tagged with HF or combination HF-UHF RFID tags (block 309) and later associated with Trackable Events in a bumping process 101 and/or Individuals using NFC-enabled devices 100. One way to begin the process is through the "bump" action 101, which illustratively involves bringing the NFC-enabled electronic device into proximity with, including right up against, the Item with RFID tag(s) that hold unique Item, Individual, and/or Order information in addition to the unique RFID number. Such Item management may include, but not be limited to, the prompt, initiation, or completion of a user action with or without the bumping action between a NFC-enabled electronic device and a uniquely identified Item by an individual or entity user. The application may also include the authentication, transmission, and reporting of the Trackable Event to authorized users on a SaaS platform in compliance with the Health Insurance Portability and Accountability Act ("HIPAA") of 1996 including protection of patient health information ("PHI") (table 212).

Illustratively, a SaaS platform may install a light software client on the NFC-enabled electronic device (block 105) to manage user actions around Trackable Events with or without wireless connectivity relying on the NFC reader electrical pulse, including, for example, pulling unique Item, Individual, and/or Order data ("Unique Data") that is embedded on the RFID tag memory 103 during the bumping action, associating the Unique Data that is pulled to the Trackable Event and storing on local file (block 201), transmitting the Trackable Event through secure socket layer ("SSL") connection between NFC-enabled electronic device and SaaS platform when one of several wireless connections are available (transmission 202), and storing Trackable Event data in its database (blocks 204 and 208). Illustratively, the SaaS platform also may authenticate the Unique Data of the RFID tag(s) with the RFID origination registry including the Item, Individual, and/or Order information embedded in the tag (table 205); may associate Trackable Event data with User Software Functionality (the software being embodied in a service, such as, for example, the Item Asset Tracking Service and the Order Adherence Service described elsewhere) (blocks 104, 105, and 207); and may report Trackable Event data to authorized users based on their Entity and Role-based access (blocks 207 and 208). Illustratively, the SaaS platform also may hold user payment information (by any payment type including credit card, debit card, electronic payment application, bank account data, and so forth) (table 207); may push payment data to a third party NFC payment device upon request in a 'bumping' transaction (block 215); may receive, if necessary, a bill from a third party device; and may enable the User to review and approve payment based on selected payment type (block 216). Such an illustrative SaaS platform may be designed and operated in compliance with all HIPAA regulations including secure data management and transmission ("SSL"), entity and role-based functional and data access, unique username and password protection with multiple security prompts, automatic system log-out after inactive time, and comprehensive transaction log (table 212).

A SaaS platform may also store and transmit relevant Individual, Item, and Trackable Event data to one or more customers in order to update their systems with relevant item tracking data (block 217). Such data may include inventory movement and/or order management information as a result of Trackable Events using Items. The SaaS may transmit such Unique Data via standard file formats (for example, Extensible Mark-up Language ("XML") or Electronic Data Interchange ("EDI")) via standard electronic communications protocols (for example, EDI, EDI INT AS2, http/s, secure FTP) in periodic batch or transactional processes based on business rules pre-established between SaaS and receiving customer entity.

Remote Storage of Trackable Event Data

The SaaS application may securely transmit the Trackable Event from the NFC-enabled electronic device to SaaS servers 203 hosted, for example, in a centralized location. The SaaS information technology infrastructure includes a generally-available firewall/load balancer 222, a web server 219 and an application server 220 to receive and process the data, and a database server 221 to store the Trackable Event data (block 204). The web server 219 manages all user engagement with the SaaS including inbound and outbound transactions. The application server 220 hosts the business objects, which receive and process transaction data by business activities such as 'adding Supply', 'decrementing Supply', recording Trackable Event data, managing Entity or User roles, generating or receiving orders. The database server 221 holds all the database fields and receives and responds to calls from the application server to receive or return data according to the aforementioned business objects functions, and related business rules.

Storage of User and Payment Information on the SaaS Platform

The SaaS platform allows User to store personal health information covered under HIPAA regulations as well as personal payment information (table 207). The User may store personal contact information, preferred provider health care information including email and cell numbers, preferred care support network including email and cell numbers, and insurance membership information. The availability of such information within the SaaS platform facilitates many functions, such as the electronic eligibility of benefits check with the insurance company, potential bill of services preceding health care service, and co-pay and deductible payment including to a third party NFC-enabled payment device (blocks 215 and 216).

Storage and Management of User Rewards on the SaaS Platform

Rewards may be managed on a SaaS platform (table 214, block 601 (FIG. 6A) and adjudicated through a NFC-device tied to completion of one or a series of Trackable Events (block 408), which may be bumping transactions 101 between a NFC-device and an RFID tag, or voice or touchscreen responses, with or without a system-generated prompt.

The SaaS platform may allow an Entity called "Rewards Manager" to add, modify, and delete various rewards with related business rules that can be linked to a user's completion of one or a series of Trackable Events for the Rewards Manager desired user performance (block 601). Such performance may be completion of a bumping transaction for a Unique Item for Trackable Event 101 such as a medical device sales representative or hospital operating room nurse bumping medical implant use for a surgery, a consumer bumping 101 a pill bottle 102 to complete a dosage event (both Trackable Events) (block 104), or touch or voice response upon his/her consumption of a medication to comply with a prescription order dosage quantity based on the Order schedule (block 513). A Rewards Manager may establish Rewards for Individual completion of one or more Trackable Events with or without an Order on the SaaS Platform (block 601, table 214). User receives Rewards (block 512) as a consequence of bumping 101 Items on RFID-equipped packages 102 with Unique Data 103 for Trackable Events (block 104). The Rewards Manager may establish the Reward type (for example, financial or non-financial), Rewards business rules (for example, rewards tied to completion of one or series of Trackable Events based on a fixed or intermittent schedule), Reward value (for example, dollar value, product or service coupon, and so forth, which may be fixed or variable by Reward type), Reward duration (date and time certain or not; user action-based), Reward communication (email, text, or regular mail), and Reward redemption (for example, mail to user address, cash payment to any bank account stored on SaaS platform, or credit or coupon value to be presented upon a future product purchase like a medication refill purchase and the like) (block 601).

The SaaS can apply Rewards based the Rewards business rules established by Rewards Manager for Individual completion of Trackable Events that may be associated with a master Order. The SaaS can receive Orders in one of several ways. The SaaS may import Orders from a third party system or generate its own Orders and send to a User directly or to a Vendor (block 613). If SaaS sends Order to vendor for fulfillment, a Vendor can fulfill the order in regular fulfillment process and then bump a RFID-equipped package 101 to associate a RFID tag with the package and activate the Order on the relevant SaaS application (block 602). An Order Issuer can also create an Order on the SaaS and SaaS can send directly to the User (block 603). User can then bump device against a NFC payment device to make payment for an Order (blocks 509 and 604) or simply bump the NFC-enabled device around Trackable Events (blocks 404 and 405) that also may be associated with a master Order (blocks 513 and 608). SaaS may prompt user with earned Rewards on the SaaS (block 610) when the User refills an existing Order or initiates a new Order on the SaaS (block 611).

RFID Tag Requisition, Fulfillment and Lifecycle Management Middleware

Figure 3A:
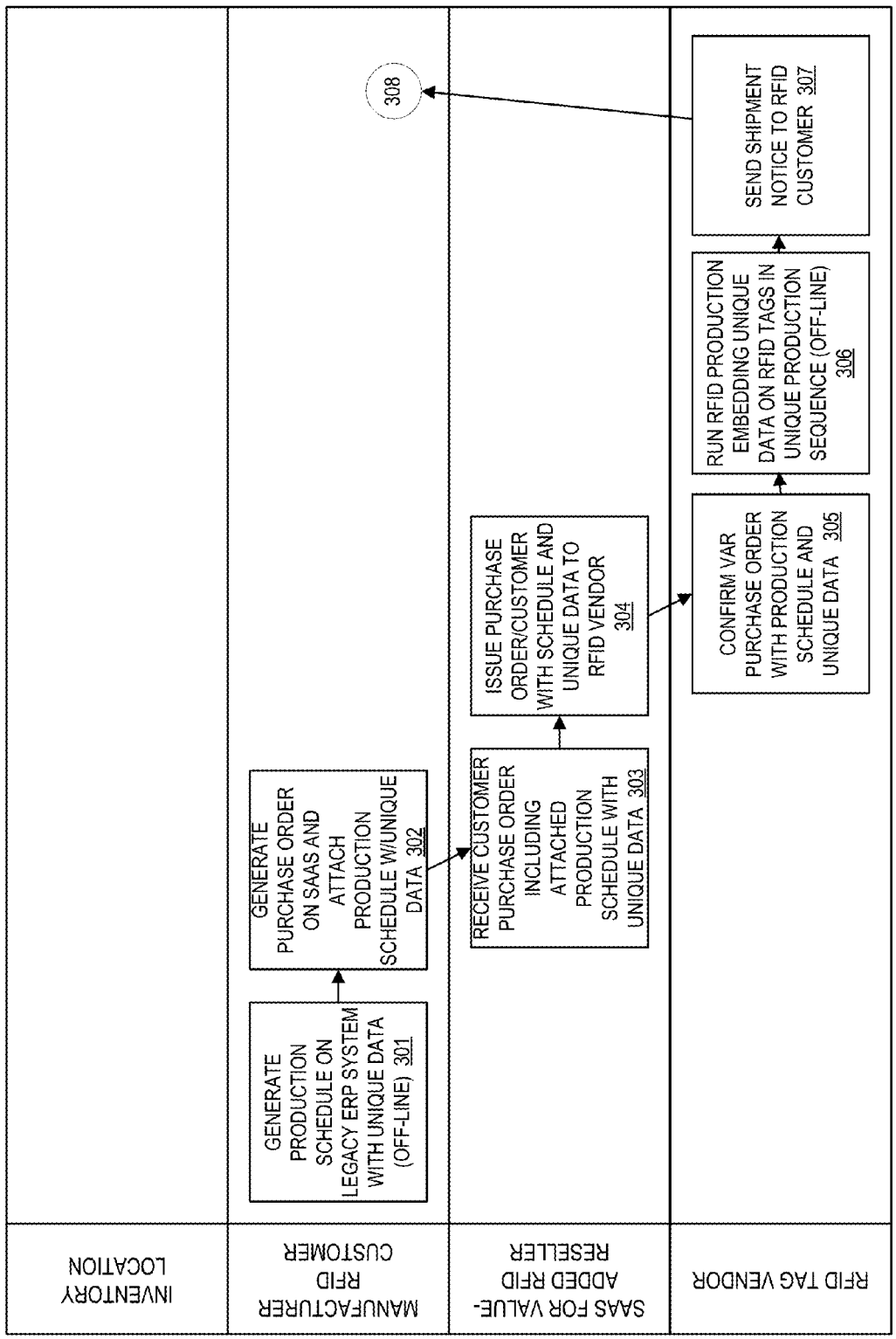
FIGS. 3A and 3B are sections of a schematic diagram of RFID tag lifecycle management software as service.
Figure 3B:
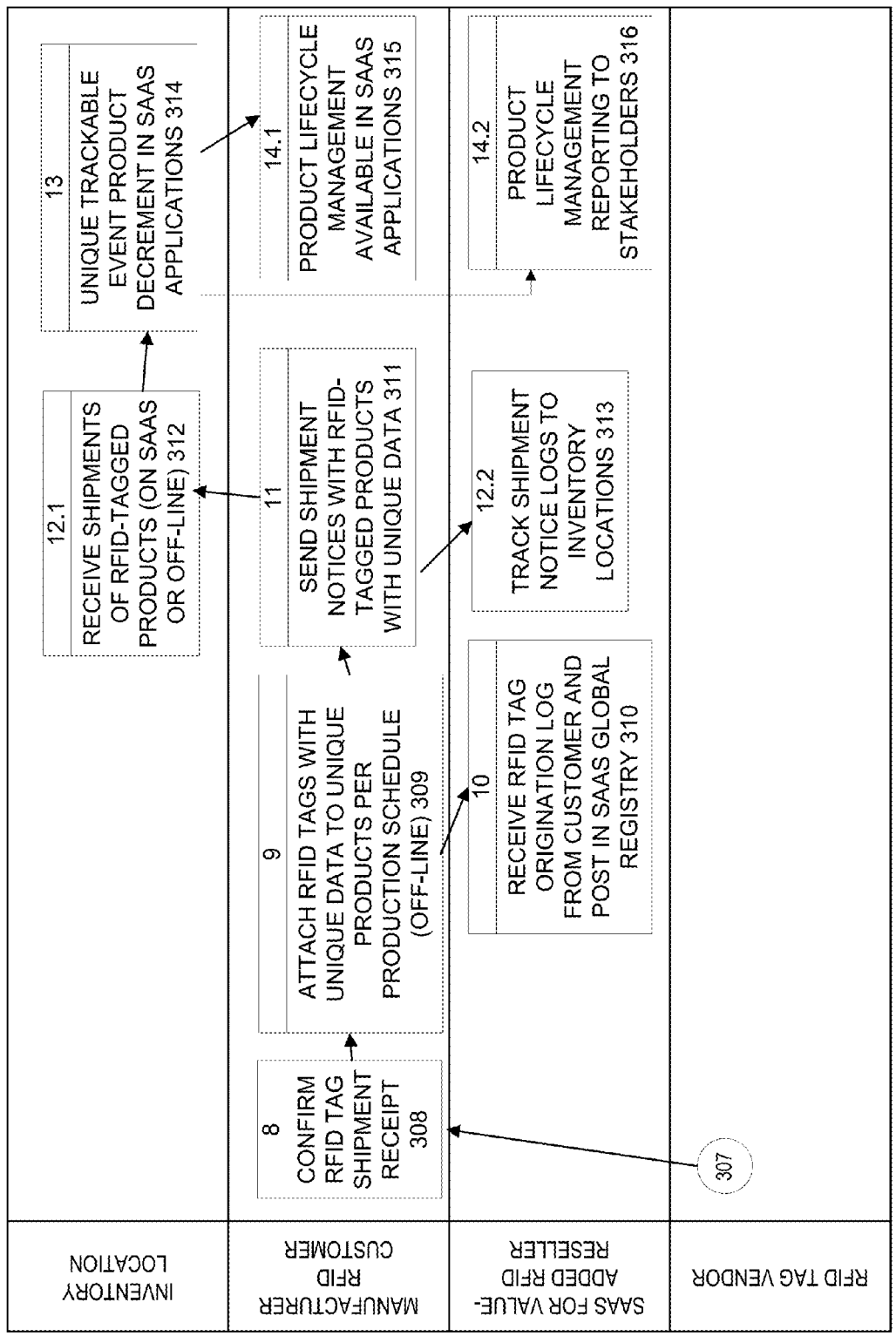

An example of RFID lifecycle management Software as a Service is shown in FIG. 3. The processes shown in FIG. 3A and 3B include the following: generate production schedule on legacy ERP system with Unique Data (off-line) (block 301); generate Purchase Order on SaaS and attach production schedule w/Unique Data (block 302), receive Customer Purchase Order including attached production schedule with Unique Data (block 303), issue Purchase Order/Customer with schedule and Unique Data to RFID Vendor (block 304), confirm VAR Purchase Order with production schedule and Unique Data (block 305), run RFID production embedding Unique Data on RFID tags in unique production sequence (off-line) (block 306), send shipment notice to RFID Customer (block 307), confirm RFID tag shipment receipt (block 308), attach RFID tags with Unique Data to Unique Products per production schedule (off-line) (block 309), receive RFID tag origination log from Customer and post in SaaS global registry (block 310), send shipment notices with RFID-tagged Products with Unique Data (block 311), receive shipments of RFID-tagged Products (on SaaS or off-line) (block 312), track shipment notice logs to Inventory Locations (block 313), Unique Trackable Event product decrement in SaaS applications (block 314), product lifecycle management available in SaaS applications (block 315), and product lifecycle management reporting to stakeholders (block 316).

An RFID middleware software suite ("RFID order fulfillment suite") integrates the production schedules of Manufacturers or Service Providers with a RFID manufacturer production schedules to enable a 1:1 relationship between a unique RFID tag number and a Unique Data Set for an Item. The SaaS platform integrates with Manufacturer or Service Provider production or Order systems to retrieve Unique product Data (block 302), receive the Customer purchase order into the SaaS platform (block 303), and present that production or order schedule to the RFID manufacturer as part of a purchase order for the RFID tags (block 304). The RFID vendor receives the uniquely-identifiable production or order schedule from the middleware system and imports into its RFID tag production system (block 305). During the production run, the RFID vendor embeds the Unique Data on the RFID tag memory section that works with SaaS application for future Trackable Event processing by consumers, businesses or government users (block 306).

Use of Different Types of RFID Tags

The Supply manufacturer may place both a HF and UHF RFID tag on the Supply item. The use of these different types of tags enables (1) wide-area, real-time (that is, within a time established by customary digital processing delays and cloud latency) inventory tracking using the UHF tags connected to third party power nodes and the NFC-enabled electronic device UHF reader, and (2) transaction management and authentication for one or more Supply Items around Trackable Events using the HF RFID tag. Since UHF tags operate in the same frequency as any mobile phone circuitry of a wireless NFC-enabled electronic device in all wireless communications formats, one way to avoid conflict is for the user to deactivate the wireless functionality on any NFC-enabled electronic device that includes mobile phone circuitry in order to use the NFC-enabled electronic device to view UHF RFID Supplies in the asset tracking SaaS noted below.

Association of RFID Tag with an Item

The RFID vendor issues a shipment notice to the middleware system of its RFID production run confirming the sequence of uniquely-identified Items (block 307), which the middleware forwards to the Supply Manufacturer production systems on the SaaS platform. The Manufacturer can confirm RFID tag shipment receipt on the SaaS platform (block 308). The Manufacturer can then place the RFID tags in their packaging process so they can be associated with its corresponding Supply item (block 309).

In one implementation, the Supply Manufacturer peels and places the RFID tag (either HF and/or UHF) on each Supply item for distribution to its business or individual customers (block 309). The Item now has a unique RFID code. The Manufacturer has option to activate the Item in the SaaS global registry using the bump method 101 with a NFC-enabled device running the client software application that provides a product activation 'bump' function. Alternatively, the RFID tag 103 now has the original manufacturing date embedded in the memory section as part of the Unique Data (block 306). The SaaS may pull this origin date, add item transfers and add the consumption date as users bump 101 the product in Trackable Events (blocks 104, 314 and 204 and table 208). In both instances, the SaaS will capture the origin date and all events associated with the Item until the consumption date (block 314, tables 208 and 205, and blocks 406, 407 and 409) and can share such lifecycle reporting with authorized stakeholders (table 205 and block 416). The SaaS platform may acknowledge and process transactions around Trackable Events by matching the unique RFID number on the Supply Item with the SaaS record of such item from the original product activation date (blocks 314, 316 and 409). Authorized stakeholders may have access to product life cycle reporting including original product activation date when Manufacturer placed RFID tag on the RFID-equipped package and activated in the SaaS platform to the Item's final consumption date (blocks 316, 416, 418, 419, and 420).

Management of Items Around Trackable Events

Below are two examples of the management of supplies around Trackable Events, one being an Item Asset Tracking service which is shown in FIGS. 4A and 4B, and the other being an Order Adherence service running on a SaaS platform which is shown in FIGS. 5A and 5B. Even though the services are different, some functional aspects are the same. Both SaaS applications may be made suitable to run on all generally available operating systems including, but not limited to RIM OS, Apple OS, Android, Palm, Microsoft Mobile, Symbian, and MeeGo. The SaaS information technology infrastructure includes a generally available firewall/load balancer 222, a web server 219 and an application server 220 to receive and process the data, and a database server 221 (block 204) to store the Trackable Event data (table 208). The web server 219 manages all user engagement with the SaaS including inbound and outbound transactions. The application server 220 hosts the business objects, which receive and process transaction data by business activities such as 'adding Supply', 'decrementing Supply', recording Trackable Event data, managing Entity or User roles, generating or receiving orders. The database server 221 holds all the database fields and receives and responds to calls from the application server to receive or return data according to the aforementioned business objects functions, and related business rules.

Figure 8B:
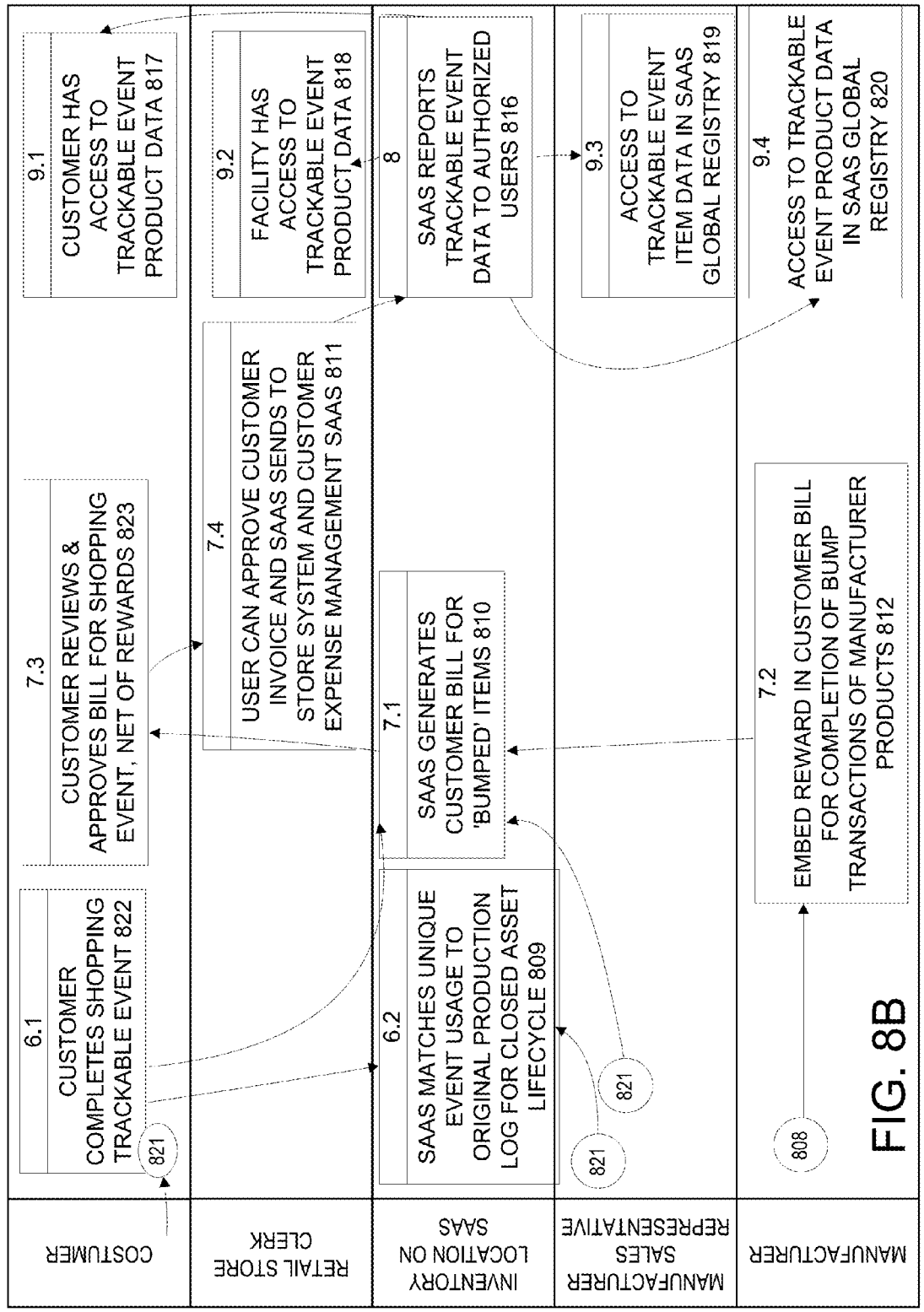
Figure 9A:
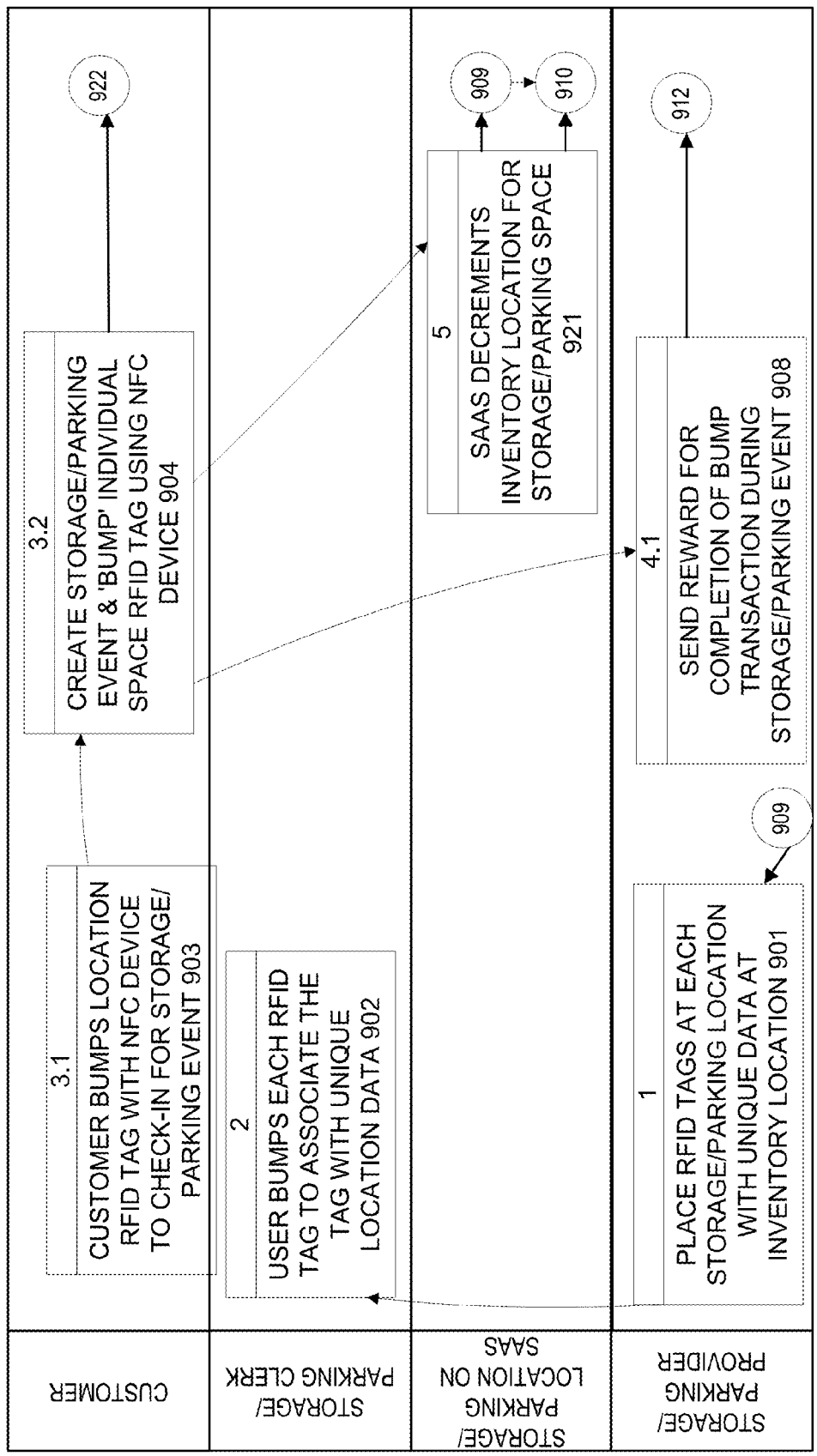
FIGS. 9A and 9B are sections of a schematic diagram of consumer storage and parking using an NFC-enabled device.
Figure 9B:
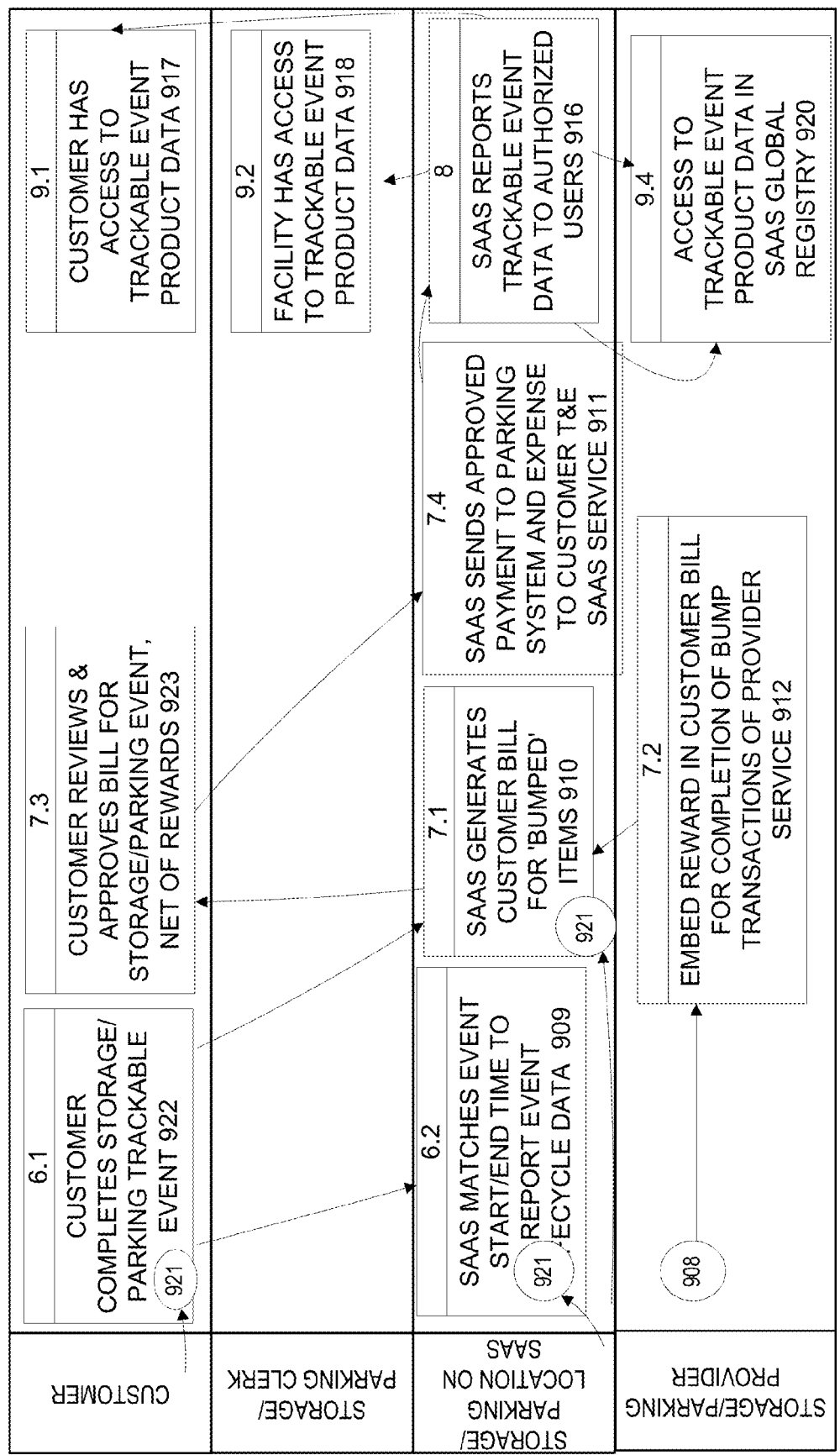

Additional examples of the management of items around Trackable Events which use in particular the event-based asset tracking and rewards management techniques described herein, are field service logistics (FIGS. 7A and 7B), consumer shopping (FIGS. 8A and 8B), and storage or parking (FIGS. 9A and 9B).

Item Asset Tracking Service

This service illustratively involves management of Items associated with Trackable Events including, but not limited, those events associated with Individuals, date, time, and location.

The role of administration in Item asset tracking includes the following.

The administration user may create Entities (Facility, Manufacturer, User, Order Issuer, Order Approver/Payer, Rewards Manager, and other), and Roles for Entity (including but not limited to Scheduler, Inventory Control Person, Manager for Facility; Sales Rep and Distributor for Manufacturer; User and Associates for User; Order Issuer and Scheduler for Order Issuer; Approver and Claim Payer for Payer; and Administrator and Account Manager for Rewards Manager). The User may create product category, sub-category, sub-category-2, or more sub-categories and associate one or more Items from one or more Manufacturers to each category.

Manufacturer administration may create users by role; create territories and associate Facilities and Users to territories; create parent Tray IDs and associate item catalog codes to parent Tray codes; create, modify, and delete Stock Locations; and upload product catalog master and Facility-specific price list.

Facility administration may create, modify, and delete users by role; create, modify, and delete Inventory Locations; add, modify, or delete par levels; upload/delete item master information against a supplier catalog master; add, modify, or delete inventory stocking information by stock type by location for each item.

Rewards Manager administrator may add, modify, or delete Account Managers; add, modify, and delete Territories and associate Clients (for example, retail locations such as a pharmacy chain, mail order distribution company, or hospital) and Account Managers to Territories; view and delete any Reward programs created and managed by Account Managers for Clients; add, modify, and delete reporting services categories (such as Trackable Event definition, Rewards program, geographic Territories, and user demographic groups); and access reporting services regarding Rewards efficacy across Clients or users.

The role of users in Item asset tracking includes the following.

An Inventory Control Person ("ICP") or Sales Representative role may create an Event or import an Event schedule from a third party application such as a Scheduling application via an XML transaction document and generally-available electronic import mechanism (e.g. VPN, EDI INT AS2) (blocks 403, 404, 405). System generates a unique event ID number. User may add, modify, delete, or view data fields including, but not limited to, unique Event ID number from third party system, Individual (for example, patient) name, date of birth, social security number, insurance company, insurance ID, Order Issuer (for example, physician) name, Order Issuer (for example, physician) ID, Event (for example, procedure) name, Event classification (for example, ICD-9/10 classification code), Event qualification (for example, procedure side like left, right, both, anterior, posterior, other), and other Individual information such as height, weight, or other user profile data. The ICP either is covered under the Patient Health Information provision of HIPAA and is authorized to see patient-identifiable data or, in case of Sales Representative, only sees and/or records de-identified data in the application.

A Facility Inventory Control Person user or Manufacturer Sales Representative may select 'Add RFID Tag' icon to enter an existing on-the-shelf item into the SaaS platform. The user peels a RFID tag from a roll and sticks on to the Supply package. The user then enters the catalog and lot/serial code information to the NFC-enabled electronic device by (1) using a generally-available bar code scanner embedded in or tethered to the NFC-enabled electronic device, or (2) manual entry, and then bumps the NFC-enabled electronic device against the RFID tag on the Item. The system associates the unique RFID tag with the Item data in the application for future Trackable Event management (block 402). The SaaS platform may generate Rewards to user based on completion of one or a series of Trackable Events using the NFC-enabled device and communicate the Reward via text, email, or call to the individual user based on the Rewards business rules (block 408).

An ICP or Sales Representative may Add or Transfer/Return Items between Locations) (blocks 406,407) by bumping 101 the NFC-enabled electronic device against one or more Supply items with RFID tags and add to the Event record. User can remove items, save, and/or complete the Event transaction (blocks 406, 407). The SaaS decrements Inventory automatically (block 421), and matches items to original product activation record to complete the asset lifecycle report sharable on the SaaS platform with authorized stakeholders (block 409).

Rewards Provider Account Manager may add, modify, or delete Clients with contact information; add, modify, or delete Rewards programs for one or more clients including (Reward type, business rules, value, duration, communication, and redemption); and add, modify, or delete reporting queries against the database to establish correlation patterns among Clients and Users based Trackable Event types, geographic location, demographic groups, or Reward programs. (block 601 (FIG. 6A), table 214).

The client-side application (block 105) stores the Trackable Event data in the NFC-enabled electronic device (block 201) and periodically transmits 202 the Data over the internet to the SaaS platform as soon as a web-enabled wireless connection is available to the NFC-enabled electronic device. The application may also work directly connected to the SaaS platform without any Client side software implementation on the NFC-enabled electronic device. Transmission may occur through generally available communication modes such as Wi-Fi, Bluetooth, wireless, or other wireless protocol. This transmission may be a batch or event-specific process.

The SaaS System may post Trackable Event data into any third party order management or manufacturer enterprise planning system 217 via a HIPAA-compliant communications protocol. An appropriate SaaS application may, for example, generate a daily Financial Order at a preset time each day of the prior twenty-four hour Supply usage by manufacturer and by Inventory Location. The Facility Manager can review, reject with reason, or approve the Financial Order(s), which the SaaS System may push into a legacy materials management system in desired transaction format (XML, EDI) and HIPAA-compliant communication protocol (e.g. HL7, EDI INT AS2, secure FTP, or http/s).

Facility and Manufacturer users may view Trackable Event data by Individual and Order Issuer (for example, Physician), and Items at each Stock Location (table 208). Manufacturer or a Customer of Manufacturer/Service Provider may import Trackable Event data and Financial Order information electronically to their own enterprise resource planning system 217 to decrement inventory based on the unique catalog, lot/serial number and the unique RFID asset tracking number.

A detailed example of event-based asset tracking using NFC-enabled devices is shown in FIGS. 4A and 4B. The processes shown in FIGS. 4A and 4B include the following: send shipment of RFID-tagged products with Unique Data to Inventory Location (block 401); SaaS updates inventory location with unique products (block 402); SaaS updates inventory location with unique products (block 421); import unique patient data to Trackable Event from Patient RFID tag (block 403); create unique event, add/import event ID, & bump product usage using NFC-enabled device (block 404); create unique event, add event ID, & bump product usage using NFC-enabled device (block 405); bump products to transfer out of inventory location (block 407); bump products to transfer out of inventory location (block 406); send rewards for completion of bump transaction (block 408); SaaS decrements inventory location for unique products (block 421); continuation to FIG. 4B; SaaS matches unique event usage to original production log for closed asset lifecycle (block 409); SaaS generates daily financial order by manufacturer for used Items (block 410); user can approve financial orders for push to legacy materials management system (block 411); user can embed Reward in financial order for completion of Bump transaction (block 412); bump products to accept/receive to inventory location (block 413); bump products to accept/receive to inventory location (block 414); SaaS increments products to inventory location (block 415); SaaS reports Trackable Event data to authorized users (block 416); Patient has access to Trackable Event product data (block 417); Facility has access to Trackable Event product data (block 418); Access to Trackable Event Item data in SaaS global registry (block 419); and access to Trackable Event product data in SaaS global registry (block 420).

Order Adherence Service ("Adherence Service")

This service illustratively involves management of Item consumption by Individuals in compliance with an Order such as a prescription order or any compliance program which has one or more Trackable Events. By way of example, an Order may be a prescription order, nutritional program, wellness program, or instructional program. An Order may have one or more specific Trackable Events that involve one or more Individuals, one or more Items, and one date, time, and geographic location. An RFID tag embedded on an Item may hold Unique Data that the SaaS will retrieve and manage for the Trackable Event associated with the Order.

Unique Data is embedded on RFID tags and Associated with an Individual using an NFC-enabled electronic device. Supply Distribution Center users place RFID tags on packages and ship RFID-equipped packages ("RFID ID Packages") to Retail Locations ("Retail Locations") such as mail-order pharmacies, retail pharmacies, nutrition stores, or any retail location in customary shipping process (block 502).

Retail Location Order Fulfillment user uses the Adherence Service running on a NFC-enabled electronic device that interfaces with their customer order fulfillment system to query and retrieve Order records in the legacy system. Various methods to associate a unique RFID code on an Item with an Order. One method enables the Order Fulfillment User using a client application on a NFC-enabled device (for example, a tablet) to query, retrieve, and import Order Unique Data information (for example, Individual name, Item name, Item quantity, Dosage quantity, dosage schedule, expiration date, number or allowed refill requests, and so forth) from the legacy order fulfillment system into the NFC-enabled device client application and then NFC device programs the RFID tag memory area with said Unique Data (blocks 504, 505). Another method repeats the first method except the client application does not program the Order Unique Data on the RFID tag. Rather, the client application simply associates the RFID code with Order in the client application (blocks 504, 505). Under both methods, the client application stores the information on the NFC-enabled device (block 201) and transmits the Order Unique Data including associated RFID code to the SaaS Adherence Service when a wireless connection becomes available (transmission 202). The User, Associates, Order Issuer, and other relevant stakeholders now have real-time (that is, within a time established by customary digital processing delays and cloud latency) Adherence reporting as Individual receives notifications from the Order in push notification, text, email or phone call based on user's preference (table 209). Another method involves a periodic import of order data from a third party order system to the SaaS platform for one or more Individuals as authorized by an Order Approver (for example, a third party health payer) for the Individual. The Adherence Service holds the Order and waits for Individual to activate the order by bumping the NFC-enabled device against the RFID-equipped package 102.

The SaaS notifies the Retail Order Fulfillment user if the Individual is already in the customer fulfillment system and the SaaS application. If customer is not in the SaaS application, the retail fulfillment user can request the customer's email address at the point of sale. The SaaS then sends the User an email with a URL to download the client application to the NFC-enabled device (block 506). The customer can download the SaaS application at the retail store with retail fulfillment user's assistance (block 507). Alternative, if dealing with a mail order distribution mechanism, the system may email the customer with a URL link to a desired web site including a unique new user code and temporary password. In any scenario, the customer can download the SaaS application running on all major NFC-enabled electronic device operating systems (RIM, Apple, Android, Palm, Symbian, MeeGo, and Microsoft Mobile non-inclusive) on their NFC-enabled electronic device through the application store of their Device vendor (block 507).

In the Order capture scenarios described above, the SaaS Platform automatically associates any available Rewards to the Order based on user Trackable Events matched against the business rules established by the Rewards Manager Account Manager at such time the user activates the Order on the SaaS Platform whether at home or at a retailer location (block 508). The Rewards Account Manager may have a work queue of outstanding Orders including Reward compliance status with Order on a mobile or desktop computing environment (block 609). The Account Manager may add, modify, or delete a Reward for an individual user (block 609).

The Adherence Service presents the Individual a personalized work queue of existing Orders including new, incomplete, and completed. User may open the order record and system may prompt user to initiate a new order and follow an Order schedule (for example, dosage events), or follow a dosage schedule on an incomplete order (block 508). The user may see any available Rewards provided by the Rewards Manager for the specific Individual Order in their own work queue (blocks 508, 512). The user may click the link and see the Rewards program and user progress towards achieving the program schedule, and perhaps the Reward value at the end. The Rewards Manager may decide to establish an intermittent Reward schedule with unknown Reward value seen by user in order to motivate user to maximize compliance with the Reward Manager's desired user behavior such as compliance with a prescription order and dosage schedule (blocks 601, 609).

The user may establish an associates ("Associates") network of other individuals (first name, last name, email address, cell phone number, and unique association question-answer for security purposes). By way of example, the Associates could be care providers (for example, physician, health coach, or therapist), family members, and/or friends who are either legally obligated or interested to follow the Individual's adherence to the Order. One possible approach to security is to challenge the caregivers with a security prompt question and add two other security question-answers to protect their account access. The system may allow caregivers to see the customer's Order adherence data and reporting history including receiving text, email, and/or phone prompts on new orders and missed dosage schedule events.

The Adherence Service integrates with customer order fulfillment systems so customer order files that are expressly tagged with RFID ID packages for individual orders (batch or real-time process) may be periodically imported to the SaaS Platform. The database carefully segregates and blinds all order transaction data sets by Customer Entity and by associated Individual customers of each Customer Entity. Once large order transaction scale is achieved, blade database servers may be dedicated for each Retail customer so there is physical server separation of Customer data sets. For illustrative purposes of FIGS. 5A and 5B, Individual Order information includes, but is not limited to, the unique RFID tag, patient name, unique patient identification, insurance company, insurance ID, physician name, medication name, medication catalog number, order quantity, dosage quantity and schedule, dosage method description, and dosage expiration date. The system may associate information regarding Item (for example, medication) related side effects, side effect response, and item interplay with other items the Individual has activated under an existing order that has not been completed.

When the user receives the RFID-equipped package, the user opens the Adherence Service on NFC-enabled device (block 105) and bumps the device 101 on the RFID-equipped package 102 until the application acknowledges the RFID number from the memory tag and authenticates the correct order between the RFID package and the Individual's order information earlier imported to the Adherence Service from the Supply Distribution order system as earlier noted (block 508). The system may then activate the Individual's order including the required consumption/dosage schedule (table 206) as well as any applicable Reward program pre-set by a Rewards Provider (block 601 and table 214). The system establishes a date, time, and geo-location record for the order activation (table 208 and block 508) and sends text and email messages to the user and authorized care providers of the user's adherence to the consumption schedule as well as progress to achieving the Reward (block 512).

If the Individual picks up an Order at a retail location, the User can make payment using the Adherence Service payment tool (block 509). The Individual "bumps" the User's NFC-enabled device against a third party NFC payment device 200. The Retail Location NFC payment device pulls User payment information and presents bill net of earned Rewards (blocks 510 and 215 and table 207). The Individual can choose the default payment or alternative payment method. The appropriate SaaS application may calculate the Individual's payment obligation for the Order based on Individual's third party Insurance eligibility of benefits information which may be stored on the User's SaaS account (block 215). The SaaS application may also apply an earned Reward for prior Adherence activity against the transaction amount on the NFC-enabled device (block 509, table 214, block 215). In the health care industry example, the Individual may be required to pay a defined co-payment or deductible for each Order. Alternatively, the Retail User may manually input the Individual payment obligation in the Adherence Service as presented by the Retail customer order fulfillment system. The Individual may review and approve the bill in the SaaS or third party NFC payment device based on the parties preferred method of payment (blocks 216, 511). If Individual approves payment on the SaaS system, the SaaS system pushes a payment voucher to the NFC payment device to process the payment transaction for the Retail location (table 210, block 511).

When the user receives a text prompt, the user may open the text and acknowledge adherence to the consumption order, and/or bump the NFC-enabled electronic device 101 against the RFID-equipped package 102 for the consumption (for example, dosage) quantity per the Order (block 513). For example, based on the business rules established by Adherence Service, if the order calls for a two item (for example, pill) consumption, the user may bump the device against the package one time to count for quantity of two or two times to count for same quantity. The system places a date, time, and geo-location stamp on every consumption transaction (table 208) and reports adherence or non-adherence to the Individual and authorized Associates by the Individual (table 209, block 512). The SaaS may automatically update the Rewards program for the Trackable Event activity in order to calculate an applicable Reward (block 609). Associates (for example, care providers) may be prompted if the user has missed a consumption/dosage event via text, phone call, or email as authorized by care providers that the user authorizes to receive such information (block 512).

The system manages the consumption quantity against the order amount, and generates a text and/or email message to the user to approve a refill request if the order calls for an Order renewal based on Order business rules (block 515). User may authorize the Order renewal (for example, refill) request, which the system sends and posts to the originating order Supply Distribution center user for Order renewal (block 517). If a new order is required (for example, a refill of prior order is not allowed), the Individual may review and approve a re-order request to the Order Issuer (for example, physician). The Order Issuer can review, approve, or reject with reason the User's refill request (block 516). The Retail Location order fulfillment user has a work queue of refill requests from authorized users. The user may accept or reject with reason the individual refill request (block 517).

If accepted, the system sends refill notice to Retail Location order fulfillment system, and the order fulfillment system including the unique RFID number is restarted for the next Supply package (blocks 517, 504).

The Adherence Service presents the user and authorized Associates robust adherence reporting in desktop and NFC-enabled electronic device environments across specific geography, medication types, and demographic populations (table 209). Users may see order history; consumption compliance history to Order; Order refill rates; item (for example, medication) interplay history when customers have one or more active Items under one or more Orders; adherence rates by geography, demographic, item type, and Individual profile (for example, medical condition); and payment transaction information (table 209).

An administration user may create, modify, and delete Entities (e.g. Company, Manufacturer, Retail, Order Issuer, Customer, RFID Vendor, and Payer) and Roles (Production Manager for Company; Production Manager for Manufacturer; Order Fulfillment for Retail; Individual and Associates for Customer; Order Issuer for Order Issuer; and Order Approver for a third party Payer if required); may administer electronic business module to receive RFID Package orders from Manufacturers, pass through orders to RFID tag vendor production system, receive shipment notices from RFID tag vendor, and received confirm shipment notice from RFID Package Manufacturer.

A manufacturer administration user may add, modify, delete users by role; create, modify, and delete Manufacturer locations; and manage e-business protocols (for example, transaction schema, communications IP address, batch or transaction, communications protocol).

A retail administration user may add, modify, delete users by role; create, modify, and delete Retail locations; create, modify, and delete Territories and associate Retail locations to Territories, and associate users to Retail Locations; and manage e-business protocols (for example, transaction schema, communications IP address, batch or transaction, communications protocol).

A RFID Vendor administration user may add, modify, delete users by role; create, modify, and delete Manufacturer locations; and manage e-business protocols (for example, transaction schema, communications IP address, batch or transaction, communications protocol).

An Order Approver (for example, Payer) administration user may add, modify, delete users by role; create, modify, and delete Territories and associate Retail locations to Territories.

A Rewards Provider administrator may add, modify, or delete Account Managers; add, modify, and delete Territories and associate Clients (for example, like a pharmacy chain/pharmacy benefit management company or hospital) and Account Managers to Territories; view and delete any Reward programs created and managed by Account Managers for Clients; add, modify, and delete reporting services categories (such as Trackable Event definition, Rewards program, geographic Territories, and user demographic groups); and access reporting services regarding Rewards efficacy across Clients or users.

A Rewards Provider Account Manager may add, modify, or delete Clients with contact information; add, modify, or delete Rewards programs for one or more clients including (Reward type, business rules, value, duration, communication, and redemption); and add, modify, or delete reporting queries against the database to establish correlation patterns among Clients and Users based Trackable Event types, geographic location, demographic groups, or Reward programs.

An Individual profile administration user may add, modify, and delete personal contact information including email and cell phone for SaaS prompts; add, modify, and delete Associate contact information from preferred physicians and care givers including email and cell phone for SaaS prompts and access; insurance company information including plan name and membership ID including authorization to electronically check eligibility of benefits for any required insurance transactions like prescription medications; and preferred payment information including, but not limited to credit card, debit card, electronic payment, or bank account ACH information.

FIGS. 5A and 5B show an example of Order Adherence Service using NFC-enabled devices. The processes shown in FIGS. 5A and 5B include the following: place RFID tags on packaging during production run (off-line) (block 501); ship RFID-tagged packages to Retail or Mail Order Pharmacy (Off-line) (block 502); order issuer/physician prescribes Order/Rx to Patient and notifies Pharmacy (off-line) (block 503): retail store user creates Order with Unique Data and User/Patient financial bill, fills package (both off-line), and bumps RFID-equipped package to associate tag and activate tracking on SaaS application (block 504); SaaS imports Order with User/patient insurance data (if relevant) from Retail Order System with Unique Data including RFID association to package (block 505); SaaS emails Patient (if willing new user) with SaaS client application URL to download to NFC-enabled device; Order User/patient downloads SaaS application and adds payment options (block 507); patient receives Order and bumps package to activate Order adherence tracking (block 508); continuation to FIG. 5B; patient bumps against NFC retail payment device to pay bill net of earned Rewards (block 509); retail NFC payment device pulls user payment information and presents bill net of earned Rewards (block 510); patient approves payment and SaaS updates patient payment records (block 511); SaaS prompts user (text, email, call) with event/dosage information and/or Rewards, and reports missed consumption to Order Issuer and Associates (block 512); patient receives dosage prompt and bumps RFID package for dosage quantity (block 513); SaaS prompts patient with refill request based on dosage adherence (block 514); patient receives prompt and approves refill request (block 515); physician receives email with patient refill request and approves refill (block 515); pharmacy receives re-fill order from Physician and executes Step 4 (block 517).

Prescription order adherence serves as a use case scenario. The example of FIG. 5 includes the ability to send Rewards to Individuals/Patients for completion of Trackable Events (block 514). The SaaS Platform of FIG. 2 may also include a Rewards reporting table 213 and a Rewards management master table 214 for key stakeholder reporting services, in addition to the other tables that may be generally used by suitable servers in the SaaS platform for key stakeholder reporting services.

The Rewards Manager Administrator and Account Manager roles may have access to the Rewards reporting table through the SaaS platform (table 214). Such a table reports user compliance per User including current Trackable Event compliance and earned Rewards per User; Rewards financial reporting at state, region, and national levels so the Rewards Provider knows the liability, financial or otherwise, of earned Rewards across the network; audit trail reporting so the Manager sees the additions, modifications, or deletions of Rewards across various time periods; and rewards compliance reporting that shows aggregate user compliance by Reward Type by rewards schedule across various demographic groups and regions so Providers can design the optimal Reward programs for specific Items and/or demographic groups.

The SaaS platform may enable a Rewards Manager, which may be a Manufacturer, Wholesaler, or Retailer, to add, modify, and delete Rewards programs for Individual Users and/or Individual Inventory Locations or Facilities for one or more Supply Items (block 601). The SaaS platform may then automatically present eligible Rewards (blocks 408, 412, 512) to authorized users and/or Inventory Locations based on user completion of one or a series of Trackable Events for Unique Items that conform to the business rules of the Rewards program (table 214). Users may have the ability to redeem the Reward as credit for a future purchase transaction that may be processed through the NFC-device payment function or as an off-line coupon (blocks 509, 511, 216).

The SaaS can apply Rewards based the Rewards business rules established by Rewards Manager for Individual completion of Trackable Events that may be associated with a master Order. The SaaS can receive Orders in one of several ways. The SaaS may import Orders from a third party system or generate its own Orders and send to a User directly or to a Vendor (block 613). If SaaS sends Order to vendor for fulfillment, a Vendor can fulfill the order in regular fulfillment process and then bump a RFID-equipped package 101 to associate a RFID tag with the package and activate the Order on the relevant SaaS application (block 602). An Order Issuer can also create an Order on the SaaS and SaaS can send directly to the User (block 603). User can then bump device against a NFC payment device to make payment for an Order (blocks 509 and 604) or simply bump the NFC-enabled device around Trackable Events (blocks 404 and 405) that also may be associated with a master Order (blocks 513 and 608). SaaS may prompt user with earned Rewards on the SaaS (block 610) when the User refills an existing Order or initiates a new Order on the SaaS (block 611).

Refer to FIGS. 6A and 6B for an example of a rewards management service using NFC-enabled devices. The processes shown in FIGS. 6A and 6B include the following: account manager adds, modifies, and deletes Rewards by Reward Type, Order Type, Trackable Event Type, User Condition Type, and/or Individual (block 601); SaaS imports Orders from 3rd party system and sends to User directly or makes available to Vendor for order activation (block 613); Order Issuer creates Order on SaaS and SaaS sends to user directly (block 612); User receives Order with RFID-equipped package and bumps package to activate Order adherence tracking (block 603); user bumps device against NFC retail payment device to pay bill net of earned Rewards (block 604); retail NFC payment device pulls user payment information and presents bill net of earned Rewards (block 605); user approves payment and SaaS updates user payment records (block 606); SaaS prompts user (text, email, call) with Event/Dosage information and/or Rewards & reports missed consumption to Order Issuer and Associates (block 607); user receives dosage prompt and bumps RFID package for Order event/dosage quantity (block 608); account manager calibrates Rewards to Individual Order adherence based on Trackable Events under Order rules (block 609); SaaS prompts user with reorder/refill request with Reward based on Event/dosage adherence under Order rules (block 610); and user receives prompt with Reward and approves which initiates Step 2.1, 2.2, or 2.3 in FIG. 6A (block 611).

Field Service Logistics

A User (e.g. Manufacturer Field Service Technician or Facility Inventory Control) possesses a NFC-enabled device that has a client software application installed on such device that enables the User to manage one or more Individual Items with Unique Data with a Trackable Event (e.g. field service repairs) at one or more inventory locations. The User may schedule a Trackable Event (e.g. field service repair event), bump the NFC-enabled device against the RFID tag embedded on a RFID-equipped product to capture Unique Data for the Item (e.g. aircraft, turbine, wastewater treatment plug, sparkplug car), and complete the Trackable Event on the application. The Service may generate a billable Order based on Item usage in Trackable Events available for a User to approve on a web or mobile application. Such Order may contain a Reward provided by a Manufacturer based on business rules regarding a Facility's usage of Items, which could be a volume and/or market share threshold for the Manufacturer and/or for Manufacturer brands of Items. Upon Order approval, the Service can send the Order into a Facility's materials management system as well as a Manufacturer's enterprise resource planning system using standard electronic business interface protocols (e.g. Electronic Data Interface (EDI), EDI INT AS2, secure FTP, http/s, and other communication protocols (block 202, 217, 223).

The Item Asset Tracking Service then transmits the Unique Data of the Used Items and Order from the device to a remotely-hosted software as service platform via wireless connection at which point the Item usage or Order data is stored in one or more database tables. The Service enables the User and other interested stakeholders to access reporting data about Items and its' Unique Data for Trackable Event through the web-based or mobile client application. Such reporting data shall be different for each Entity and Role based on their access rights and data requirements.

Certain users have the ability to use the NFC-enabled device and client application to transfer Items among one or more inventory locations (each such transfer being a Trackable Event with user, date, time, and geo-location) including from original point of manufacture ending with the point of consumption. The Service provides complete Item lifecycle reporting of each Trackable Event with Item Usage from point of Item manufacture to Item consumption to each authorized Entity's roles.

The role of administration in Item asset tracking includes the following.

The Service Administration User may create Entities (Customer, Manufacturer, Rewards Manager, and other), and Roles for Entity (including but not limited to Scheduler, Inventory Control Person, and Facility Manager for Customer; Field Service Technician and Distributor for Manufacturer; and Administrator and Account Manager for Rewards Manager). The Administration User may create product category, sub-category, sub-category-2, or more sub-categories and associate one or more Items from one or more Manufacturers to each category in order to provide sales and market share Item data to Customer and Manufacturer Users.

Manufacturer administration may create users by role; create territories and associate Facilities and their own Users to territories; create parent Tray IDs and associate item catalog codes to parent Tray codes; create, modify, and delete Stock Locations; and upload product catalog master and Facility-specific price list.

Customer Facility administration may create, modify, and delete users by role; create, modify, and delete Inventory Locations (for example, automotive repair shop stock location, aircraft maintenance spare parts inventory location, power utility spare parts inventory location, etc.); add, modify, or delete par levels; upload/delete item master information against a supplier catalog master; and add, modify, or delete inventory stocking information by stock type by location for each item.

Rewards Manager administrator may add, modify, or delete Account Managers; add, modify, and delete Territories and associate Clients and Account Managers to Territories; view and delete any Reward programs created and managed by Account Managers for Clients; add, modify, and delete reporting services categories (such as Trackable Event definition, Rewards program, geographic Territories, and user demographic groups); and access reporting services regarding Rewards efficacy across Clients or users.

The role of users in Item asset tracking includes the following.

A Customer Inventory Control Person ("ICP") or Field Service Technician role may create an Event or import an Event schedule from a third party application such as a Scheduling application via an XML transaction document and generally-available electronic import mechanism (e.g. VPN, EDI INT AS2) (blocks 703, 704, 705). System generates a unique event ID number. User may add, modify, delete, or view data fields including, but not limited to, unique Event ID number from third party system; Individual (for example, customer) name, Customer ID number; Order Issuer (for example, Customer Facility Manager) name; Order Issuer name (for example, Customer Procurement Manager); Event (for example, field service repair) name; Event classification (for example, industry classification code); Event qualification (for example, rear or front bumper, left wing of aircraft), and other Individual Customer information such as profile data. The ICP and Field Service Technician is authorized to see customer-identifiable data, anonymized as needed.

A Facility Inventory Control Person user or Manufacturer Field Service Technician may select 'Add RFID Tag' icon to enter an existing on-the-shelf item into the SaaS platform. The user peels a RFID tag from a roll and sticks on to the Supply package. The user then enters the catalog and lot/serial code information to the NFC-enabled electronic device by (1) using a generally-available bar code scanner embedded in or tethered to the NFC-enabled electronic device, or (2) manual entry, and then bumps the NFC-enabled electronic device against the RFID tag on the Item. The system associates the unique RFID tag with the Item data in the application for future Trackable Event management (block 702). The SaaS platform may generate Rewards to user based on completion of one or a series of Trackable Events using the NFC-enabled device and communicate the Reward via text, email, or call to the individual user based on the Rewards business rules (block 708).

An ICP or Field Service Technician may Add or Transfer/Return Items between Locations) (blocks 706,707) by bumping 101 the NFC-enabled electronic device against one or more Supply items with RFID tags and add to the Event record. User can remove items, save, and/or complete the Event transaction (blocks 706, 707). The SaaS decrements Inventory automatically (block 721), and matches items to original product activation record to complete the asset lifecycle report sharable on the SaaS platform with authorized stakeholders (block 709).

Rewards Provider Account Manager may add, modify, or delete Clients with contact information; add, modify, or delete Rewards programs for one or more clients including (Reward type, business rules, value, duration, communication, and redemption); and add, modify, or delete reporting queries against the database to establish correlation patterns among Clients and Users based Trackable Event types, geographic location, demographic groups, or Reward programs. (block 601 (FIG. 6A), table 214).

The client-side application (block 105) stores the Trackable Event data in the NFC-enabled electronic device (block 201) and periodically transmits 202 the Data over the internet to the SaaS platform as soon as a web-enabled wireless connection is available to the NFC-enabled electronic device. The application may also work directly connected to the SaaS platform without any Client side software implementation on the NFC-enabled electronic device. Transmission may occur through generally available communication modes such as Wi-Fi, Bluetooth, wireless, or other wireless protocol. This transmission may be a batch or event-specific process.

The SaaS System may post Trackable Event data into any third party order management or manufacturer enterprise planning system (block 217,223) via a HIPAA-compliant communications protocol. An appropriate SaaS application may, for example, generate a daily Order at a preset time each day of the prior twenty-four hour Item usage by Manufacturer and by Inventory Location. The Customer Facility Manager can review, reject with reason, or approve the Financial Order(s), which the SaaS System may push into a legacy materials management system in desired transaction format (XML, EDI) and HIPAA-compliant communication protocol (e.g. HL7, EDI INT AS2, secure FTP, or http/s) (block 202, 217, 223).

Facility and Manufacturer users may view Trackable Event data by Individual and Customer Facility Manager, and Items at each Stock Location (table 208). Customer or Manufacturer may import Trackable Event data and Financial Order information electronically to their own enterprise resource planning system 217 to decrement inventory based on the unique catalog, lot/serial number and the unique RFID asset tracking number.

Figure 7A:
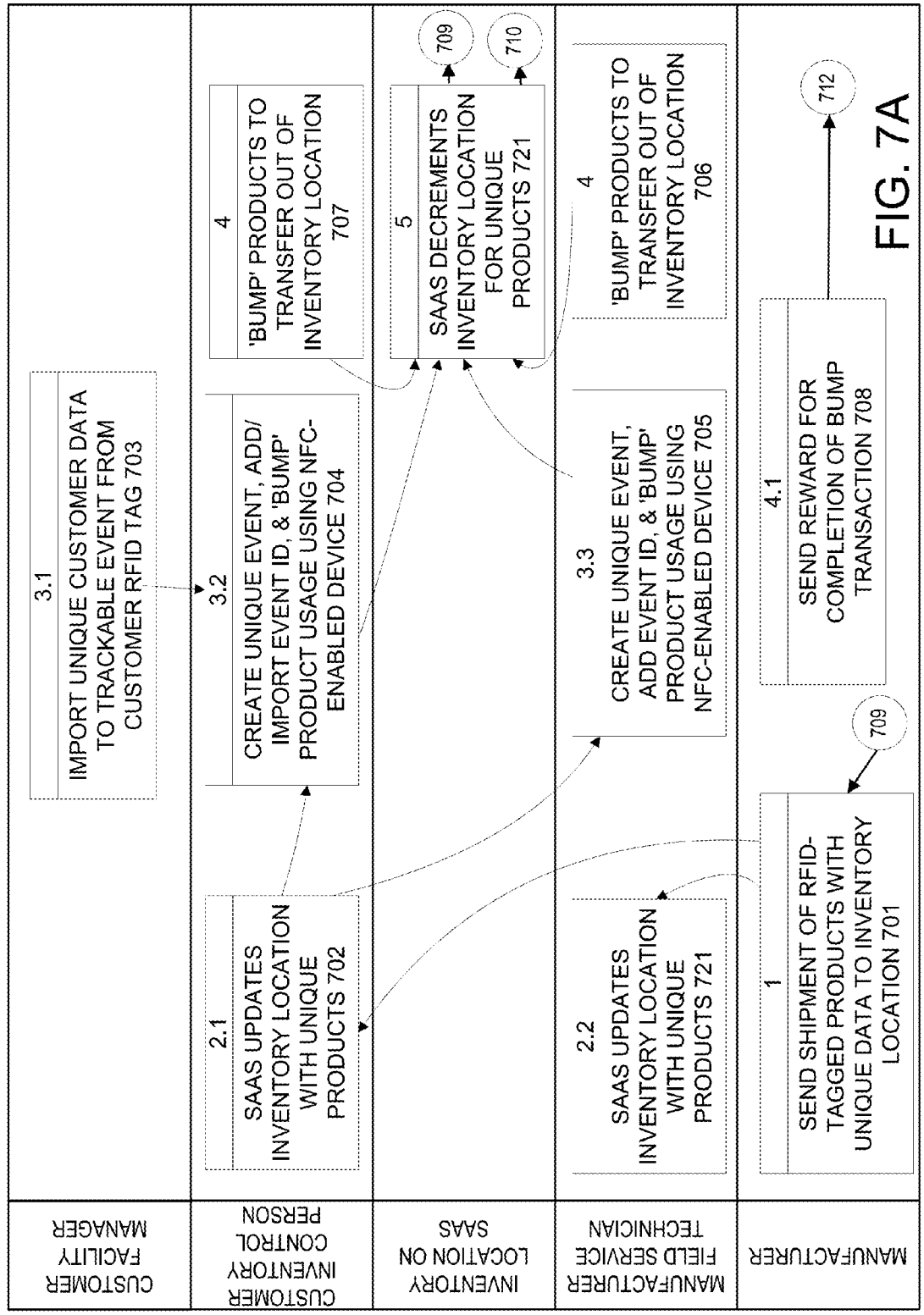
FIGS. 7A and 7B are sections of a schematic diagram of field service logistics using an NFC-enabled device.
Figure 7B:
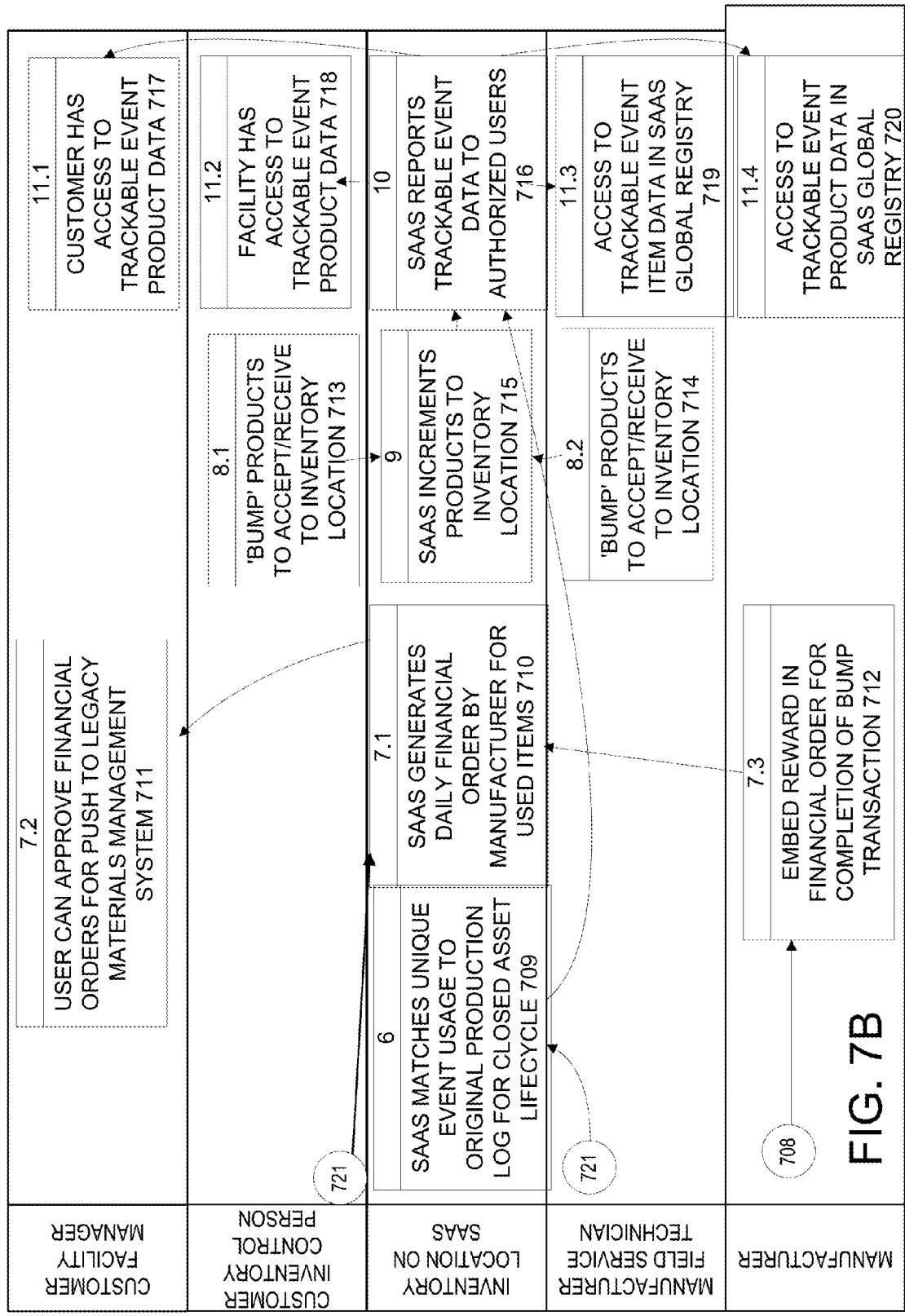

Event-based asset tracking using NFC-enabled devices is shown in FIGS. 7A and 7B. The processes shown in FIGS. 7A and 7B include the following: send shipment of RFID-tagged products with Unique Data to Inventory Location (block 701); SaaS updates inventory location with unique products (block 702); SaaS updates inventory location with unique products (block 721); SaaS imports unique Customer data to Trackable Event from Customer RFID identification tag if necessary to identify a Customer User (block 703); Inventory Control Person creates unique event, SaaS creates Event ID, & User bumps product usage using NFC-enabled device (block 704) for Trackable Event; Field Service Technician creates unique event, SaaS creates event ID, & User bumps product usage using NFC-enabled device (block 705); ICP bumps products to transfer out of inventory location (block 707); Field Service Technician bumps products to transfer out of inventory location (block 706); Rewards Manager automatically sends rewards for completion of bump transaction based business rules for Customer item usage (block 708); SaaS decrements inventory location for unique products (block 721); continuation to FIG. 7B; SaaS matches unique event usage to original production log for closed asset lifecycle (block 709); SaaS generates daily financial order by manufacturer for used Items (block 710); Customer Facility Manager approves financial orders which SaaS pushes to legacy Customer materials management system (block 217, 223, 711); SaaS can embed Reward in financial order for Customer completion of one or more Bump transactions (block 712); ICP bumps products to accept/receive to inventory location (block 713); Field Service Technician bumps products to accept/receive to inventory location (block 714); SaaS increments products to inventory location (block 715); SaaS reports Trackable Event data to authorized users (block 716); Customer has access to Trackable Event product data (block 717); Inventory Control User has access to Trackable Event product data (block 718); Field Service Technicians has access to Trackable Event Item data in SaaS global registry (block 719); and Manufacturer or Distributor has access to Trackable Event product data in SaaS global registry (block 720).

Consumer Retail Shopping

A User (e.g. Consumer) possesses a NFC-enabled device that has a client software application installed on such device that enables the User to track their shopping basket of one or more Individual Items with Unique Data around a Trackable Event (e.g. shopping) at one or more inventory locations (e.g. retail stores). The User may bump the NFC-enabled device against an RFID tag at an Inventory Location (e.g. retail store) to authenticate the User at the Inventory Location (e.g. store location) which may qualify the User to receive for Rewards provided by Inventory Location (e.g. retailer). The User may also bump the NFC-enabled device against the RFID tag embedded on a RFID-equipped Item or stock location next to the Items to capture Unique Data for the Item (e.g. catalog code; item description; retailer item price; manufacturer name; manufacturer location, date, and time; product features (such as calories/serving, servings/package, ingredients, daily allowance percentages), and other data; and complete the Trackable Event (e.g. shopping event) on the application.

The Item Asset Tracking Service can then transmit the Unique Data from the device to a remotely-hosted software as service platform via wireless connection at which point the data is stored in one or more database tables. The Service will match the Trackable Event Item Data to a product catalog master managed by each Retail Location. Such match would key on the product catalog code and unique RFID code on the product box or at the product stock location. The match would reference the other product data in the catalog master such as item description, item price, and product features. The Service automatically generates a Shopping Bill and presents the Bill to the Retail Store Clerk and User on the client software application that runs on each User's NFC-enabled device. The Service may present a Reward to the Customer based on the Customer's purchasing volume at the Retail Location and/or loyalty to a specific manufacturer or brand. The Retail Store Clerk will have access to the Service on a NFC-enabled device that will present a Customer's Shopping Bill including Individual Item Unique Data and any Customer earned Rewards for one or more items. The Store Clerk will have the ability to review and approve the Bill to Customer matched and may do a visual physical check-out of the Customer products at a check-out place in the store. Store Clerk can add, modify, or delete from the Customer Bill on the Service through manual action (check or uncheck a box) or, if products contain RFID labels, bump the NFC device and add or delete the Item from the Customer Bill. Store Clerk can approve the final Customer Bill, and present to the Customer at the check-out area of the retail store. The Customer can then review and approve the Bill on their NFC-Device and automatically approve payment using a 3rd party NFC payment service, such as Pay with ISIS or Google Wallet, which may be embedded in the Service with a single-sign capability using the OAUth2 protocol.

The Service enables the Customer, Retailer, and other interested stakeholders to access reporting data about Customer's Trackable Events including Bills of Items and their Unique Data on either web or mobile applications. Such reporting data shall be different for each Customer and Retailer based on their access rights and data requirements.

Certain Retailer Users shall have the ability to use the NFC-enabled device and client application to transfer Items among one or more inventory locations (each such transfer being a Trackable Event with user, date, time, and geo-location) including from original point of manufacture ending with the point of consumption. The Service provides complete Item lifecycle reporting of each Trackable Event from point of manufacture to consumption to each authorized Entity's roles.

The role of administration in Item asset tracking includes the following.

The Service master administration user may create Entities (Retailer, Manufacturer, Customer, Rewards Manager, and other), and Roles for Entity (including but not limited to Inventory Control Person, Administrator, and Store Clerk for Retailer; Inventory Control Person, Sales Rep, Distributor, and Administrator for Manufacturer; Customer for Customer; and Administrator and Account Manager for Rewards Manager). The Service Administration User may create product category, sub-category, sub-category-2, or more sub-categories and associate one or more Items from one or more Manufacturers to each category.

Manufacturer/Distributor administration may create users by role; create territories and associate Retail Locations and Users to territories; create, modify, and delete master product catalog and item price file for one or more Retail Customers and Retail Stock Locations; create, modify, and delete Retailer Stock Locations; and upload product catalog master and Retail Location-specific price list.

Retailer administration may create, modify, and delete users by role; create, modify, and delete Inventory Locations (for example, Best Buy 1st Avenue Retail Store, 101 1st Avenue, Rochester, N.Y. XXXXX); add, modify, or delete par levels for manufacturer items; upload/delete item master information against a supplier catalog master; add, modify, or delete inventory stocking information by stock type by location for each item; and add, modify, or delete manufacturer pricing information.

Rewards Manager administrator may add, modify, or delete Account Managers; add, modify, and delete Territories and associate Clients and Account Managers to Territories; view and delete any Reward programs created and managed by Account Managers for Clients; add, modify, and delete reporting services categories (such as Trackable Event definition, Rewards program, geographic Territories, and user demographic groups); and access reporting services regarding Rewards efficacy across Clients or users. The Rewards Manager Entity may be embedded in a Retailer or Manufacturer/Distributor Entity as needed by each Entity.

The role of users in Item asset tracking includes the following.

A Manufacturer, Distributor, or Sales Representative role may bump products onto a shipment and send to a Retailer Location (block 801). System generates a unique event ID number for the Shipment Trackable Event. A Retailer Inventory Control Person can receive a shipment by bumping the Items using the NFC-enabled device running the client application. The Service would match the shipment receipt to the original order and increment inventory on the Service. The Service would notify Manufacturer/Distributor of any back order items and return any extra items (block 802).

A Retailer Inventory Control Person user or Manufacturer Sales Representative may select 'Add RFID Tag' icon on the Service in order to enter an existing on-the-shelf item into the Service. The user peels a RFID tag from a roll and sticks on to the Item package. The user then enters the catalog code to the NFC-enabled electronic device by (1) using a generally-available bar code scanner embedded in or tethered to the NFC-enabled electronic device, or (2) manual entry, and then bumps the NFC-enabled electronic device against the RFID tag on the Item. The system associates the unique RFID tag with the Item data in the application for future Trackable Event management (block 802).

A Customer user may add, modify, and delete their personal contact information, username and password as well as preferred payment information for Bills. The Service shall support debit and credit payment, as well as NFC payment using a third party NFC payment service embedded in the Item Asset Tracking Service using single sign functionality following OAuth2 protocol. A Customer may add, modify, and delete third party expense management Software as Service vendor account information so the Service can automatically push Customer Bills to such expense management vendor when user completes a Billable Trackable Event and approves the Bill for payment.

A Rewards Provider Account Manager may add, modify, or delete Retailer Clients with contact information; add, modify, or delete Rewards programs for one or more Clients including (Reward type, business rules, value, duration, Client or Customer reward communication, and reward redemption); and add, modify, or delete reporting queries against the database to establish correlation patterns among Clients and Customers based on Trackable Events, geographic location, demographic groups, or Reward programs. (block 601 (FIG. 6A), table 214). The Service can apply Rewards when Customer completes a Trackable Event at a Retail Location (FIG. 8B, block 812) based on the aforementioned business rules for one or more Clients, and their Customer Trackable Event (e.g. shopping) data.

A Customer user may initiate a shopping trackable event (block 803) by checking in at the Retailer Location. User can bump their NFC device to the Retail Location official RFID tag check-in to activate the shopping event. Customer can then start shopping by adding items to their shopping cart on the Service. User bumps the NFC-device against the RFID-equipped Item(s) or the RFID tag price tag underneath the product shelf space (block 804). The Service matches the unique RFID code of the Item to the similar record on the Retailer's product catalog master managed on the Service and decrements inventory from the product location as the customer shops (block 821). Customer completes their shopping event (block 822). The Service matches the completed Bill of Items against the Retailer catalog master for ePedigree reporting (block 809) and automatically generates a Customer bill for the bumped Items (block 810). The Service applies any earned Rewards from the Rewards Manager (which could be a Manufacturer or Retailer) based on the Customer's aggregate purchasing volume and/or retailer or manufacturer loyalty over a period of time (block 812). The Customer can see the final Bill with the Unique Data from the Items including Item Price and any Reward discounts. Customer reviews and approves the Bill (block 823) and has the option to approve payment using a third party NFC electronic payment service, which may be embedded in the Service (e.g. Google Wallet or ISIS payment) (blocks 215, 216). The Retail Store Clerk can accept the Customer's approved Bill payment and the Service will send the approved Customer payment into the Retailer legacy accounting system as well as the Customer's expense management software as service vendor account (block 811).

The client-side application (block 105) stores the Trackable Event data in the NFC-enabled electronic device (block 201) and periodically transmits 202 the Data over the internet to the SaaS platform as soon as a web-enabled wireless connection is available to the NFC-enabled electronic device. The application may also work directly connected to the SaaS platform without any Client side software implementation on the NFC-enabled electronic device. Transmission may occur through generally available communication modes such as Wi-Fi, Bluetooth, wireless, or other wireless protocol. This transmission may be a batch or event-specific process.

The SaaS System may post Trackable Event data into any third party order management or manufacturer enterprise planning system 217 via a HIPAA-compliant communications protocol. An appropriate SaaS application may, for example, generate a Customer Bill when Customer completes a Trackable Event. The Retail Store Clerk can review, modify, or approve. (block 811). The SaaS System may push into a legacy retailer accounting system in desired transaction format (XML, EDI) and HIPAA-compliant communication protocol (e.g. HL7, EDI INT AS2, secure FTP, or http/s).

Retailer and Manufacturer users may view Customer Trackable Event data including Customer Bill of Items by Customer and Retailer at each Stock Location (table 208, blocks 816,817,818, and 819). Manufacturer or a Retailer may import authorized Trackable Event data (with proper Customer confidentiality protections) information electronically to their own enterprise resource planning system 217 to decrement inventory based on the unique catalog, lot/serial number and the unique RFID asset tracking number.

Event-based asset tracking using NFC-enabled devices is shown in FIGS. 8A and 8B. The processes shown in FIGS. 8A and 8B include the following: Manufacturer/Distributor sends shipment of RFID-tagged products with Unique Data to Inventory Location (block 801); Retailer Inventory Control person receives shipment with bump transaction and SaaS updates inventory location with unique products (block 802); SaaS updates inventory location with unique products (block 821); Customer checks-in at retailer stock location with bump action to retailer location RFID tag (block 803); Customer creates unique shopping event & bump product usage using NFC-enabled device (block 804); SaaS decrements inventory location for unique products as Customer shops (block 721); continuation to FIG. 8B (block 822, 809, 810); complete trackable shopping event (block 822); SaaS matches bumped products against catalog master for ePedigree reporting (block 809); SaaS generates Customer Bill for bumped Items with Item Price (block 810); SaaS adds Reward to Customer Bill based on Rewards business rules (block 812); Customer reviews and approves Bill with earned Rewards (block 823) and uses NFC payment option (block 200, 201, 215, 216); Retail Store Clerk Bill accepts payment and Saas routes Trackable Event Bill data to legacy accounting system (block 217, 223, 811); SaaS reports Trackable Event data to authorized users (block 816); Customer has access to Trackable Event product data (block 817); Retailer has access to Trackable Event product data (block 818); Manufacturer and Distributor Sales Rep has access to Trackable Event Item data in SaaS global registry (block 819); and Manufacturer and Distributor has access to Trackable Event product data in SaaS global registry (block 820).

Consumer Storage or Parking Service

A User (e.g. Consumer) possesses a NFC-enabled device that has a client software application installed on such device that enables the User to track a storage or parking Trackable Event (e.g. storing products or parking a vehicle) of an Individual Item (e.g. a piece of equipment, product, or vehicle) at one or more inventory locations (e.g. storage or parking locations). The User may bump the NFC-enabled device at an Inventory Location (e.g. storage or parking facility) RFID tag to authenticate the User is physically at the at the Inventory Location (e.g. storage or parking facility) and to activate a Trackable Event with date, time, user, and geo-location stamp. Such authenticated check-in may qualify the User for Rewards provided by Inventory Location (e.g. storage or parking provider) based on prior User usage of Items (e.g. storage or parking space) in prior Trackable Events. The User may bump the NFC-enabled device against the RFID tag embedded on a RFID-equipped stock location (e.g. unique storage or parking location) to capture Unique Data for the Item (e.g. catalog code; item description; provider item price; any space features. The User can then bump the RFID tag at the stock location (e.g. storage or parking space) to complete the Trackable Event (e.g. storage or parking event) on the application. The Item Asset Tracking Service then generates a Customer Bill for the Trackable Event (the check-in date and time and the check-out date and time multiplied by billing rate based on the business rules for the inventory location (e.g. storage or parking space). The Customer can review and approve the Bill on the NFC-enabled device and approve payment to Provider using an electronic payment mechanism (e.g. debit or credit card) that is linked to the Customer's Service Account.

The Service can then transmit the Unique Data from the device to a remotely hosted software as service platform via wireless connection at which point the data is stored in one or more database tables. The Service may also send the Customer Bill directly to a Customer Travel & Expense Software as a Service vendor, which can post the Storage or Parking Trackable Event Bill directly into the Customer's personal account. The Service will match the Trackable Event Item Data to a product catalog master managed by each Retail Location. Such match would key on the product catalog code and unique RFID code on the storage or parking location. The match would reference the other product data in the catalog master such as item description, item price, and product features. The Service automatically generates a storage/parking Bill when the user completes the Trackable Event by bumping the NFC-device against the RFID tag at storage/parking location and presents to User on the client software application that runs on Customer's NFC-enabled device. The Service may present a Reward to the Customer based Rewards Manager business rules such as the Customer's purchasing volume at the Storage/Parking Location and/or loyalty to a specific storage/parking provider brand. The Customer can then review and approve the Bill on their NFC-Device and has the option to automatically approve payment using a 3rd party payment service, which may include NFC, or debit or credit card linked by Customer to their own account.

The Service enables the Customer, Storage/Parking Provider, and other interested stakeholders to access reporting data about Customer's Trackable Events including Bills and their Unique Data on either web or mobile applications. Such reporting data shall be different for each Customer and Storage/Parking Provider based on their access rights and data requirements.

Certain Storage/Parking Provider Users (e.g. Storage/Parking Clerk) shall have the ability to use the NFC-enabled device and client application to place RFID tags at one or more Storage or Parking Locations. The Service provides complete Item lifecycle reporting of each Trackable Event from point of manufacture to consumption to each authorized Entity's roles.

The role of administration in Item asset tracking includes the following.

The Service master administration user may create Entities (Storage/Parking Provider, Customer, Rewards Manager, and other), and Roles for Entity (including but not limited to Clerk and Administrator for Storage/Parking Provider; Customer for Customer; and Administrator and Account Manager for Rewards Manager). The master Administration User may create product category, sub-category, sub-category-2, or more sub-categories and associate one or more Items from one or more Manufacturers to each category.

Storage/Parking administration may create, modify, and delete users by role; create, modify, and delete Inventory Locations (for example, Best Parking 1st Avenue Retail Store, 101 1st Avenue, Rochester, N.Y. XXXXX); add, modify, or delete inventory information; upload/delete item master information against a supplier catalog master; add, modify, or delete inventory information by stock type by location for each item; and add, modify, or delete manufacturer pricing information. Different storage or parking locations may be owned or leased by one or more third parties.

Rewards Manager administrator may add, modify, or delete Account Managers; add, modify, and delete Territories and associate Clients and Account Managers to Territories; view and delete any Reward programs created and managed by Account Managers for Clients; add, modify, and delete reporting services categories (such as Trackable Event definition, Rewards program, geographic Territories, and user demographic groups); and access reporting services regarding Rewards efficacy across Clients or users. The Rewards Manager Entity may be embedded in a Retailer or Manufacturer/Distributor Entity as needed by each Entity.

The role of users in Item Asset Tracking Service includes the following.

A Storage/Parking Provider may bump RFID products onto a shipment and send to a Storage/Parking Location (block 801). System generates a unique event ID number for the Shipment Trackable Event. A Clerk can receive a shipment by bumping the Items using the NFC-enabled device running the client application. The Service would match the shipment receipt to the original order and increment inventory on the Service. The Service would notify Manufacturer/Distributor of any back order items and return any extra items (block 802).

A Customer user may add, modify, and delete their personal contact information, username and password as well as preferred payment information for Bills. The Service shall support debit and credit payment, as well as NFC payment using a third party NFC payment service embedded in the Item Asset Tracking Service using single sign functionality following OAuth2 protocol. A Customer may add, modify, and delete third party expense management Software as Service vendor account information so the Service can automatically push Customer Bills to such expense management vendor when user completes a Billable Trackable Event and approves the Bill for payment.

A Clerk may select 'Add RFID Tag' icon on the Service in order to enter an existing on-the-shelf item into the SaaS Service. The user peels a RFID tag from a roll and sticks on to the Item package. The user then enters the catalog code to the NFC-enabled electronic device by (1) using a generally-available bar code scanner embedded in or tethered to the NFC-enabled electronic device, or (2) manual entry, and then bumps the NFC-enabled electronic device against the RFID tag on the Item. The system associates the unique RFID tag with the Item data in the application for future Trackable Event management (block 802).

A Rewards Provider Account Manager may add, modify, or delete Retailer Clients with contact information; add, modify, or delete Rewards programs for one or more Clients including (Reward type, business rules, value, duration, Client or Customer reward communication, and reward redemption); and add, modify, or delete reporting queries against the database to establish correlation patterns among Clients and Customers based on Trackable Events, geographic location, demographic groups, or Reward programs. (block 601 (FIG. 6A), table 214). The Service can apply Rewards when Customer completes a Trackable Event at a Retail Location (FIG. 8B, block 912) based on the aforementioned business rules for one or more Clients, and their Customer Trackable Event (e.g. parking/storage) data.

A Customer user may initiate a storage/parking trackable event (block 903) by checking in at the Storage/Parking Location. User can bump their NFC device to the Retail Location official RFID tag check-in to activate the parking event. Customer can then check-in to Unique Storage/Parking location by bumping the NFC-device against the RFID-equipped Item(s) at the storage/parking space (block 904). The Service matches the unique RFID code of the Item to the similar record on the Provider's product catalog master managed on the Service and decrements inventory (e.g. storage or parking availability) from the inventory location as the customer stores/parks (block 921). Customer completes their parking event (block 922). The Service matches the completed Bill of Items against the Provider catalog master for ePedigree reporting (block 909) and automatically generates a Customer bill for the bumped Items (block 910). The Service applies any earned Rewards from the Rewards Manager (which could be a Manufacturer or Retailer) based on the Customer's aggregate purchasing volume and/or retailer or manufacturer loyalty over a period of time (block 912). The Customer can see the final Bill with the Unique Data from the Items including Item Price and any Reward discounts. Customer reviews and approves the Bill (block 923) and has the option to approve payment using a third party NFC electronic payment service, which may be embedded in the Service (e.g. Google Wallet or ISIS payment) (blocks 215, 216). The Service will send the approved Customer payment into the legacy accounting system for the Provider as well as the Customer's expense management software as service vendor account (block 217, 223, 911).

The client-side application (block 105) stores the Trackable Event data in the NFC-enabled electronic device (block 201) and periodically transmits 202 the Data over the internet to the SaaS platform as soon as a web-enabled wireless connection is available to the NFC-enabled electronic device. The application may also work directly connected to the SaaS platform without any Client side software implementation on the NFC-enabled electronic device. Transmission may occur through generally available communication modes such as Wi-Fi, Bluetooth, wireless, or other wireless protocol. This transmission may be a batch or event-specific process.

The SaaS System may post Trackable Event data into any third party order management or manufacturer enterprise planning system 217 via a HIPAA-compliant communications protocol. An appropriate SaaS application may, for example, generate a Bill when Customer completes a Trackable Event. The Clerk can review, modify, or approve the Bill. (block 811). The SaaS System may push into a legacy retailer accounting system in desired transaction format (XML, EDI) and HIPAA-compliant communication protocol (e.g. HL7, EDI INT AS2, secure FTP, or http/s) (block 217, 223).

Storage/Parking Provider and Manufacturer users may view Customer Trackable Event data including Customer Bill of Items by Customer and Retailer at each Stock Location (table 208, blocks 916,917,918, and 919). Storage Provider may import authorized Trackable Event data (with proper Customer confidentiality protections) information electronically to their own enterprise resource planning system 217 to decrement inventory based on the unique catalog, lot/serial number and the unique RFID asset tracking number.

Event-based asset tracking using NFC-enabled devices is shown in FIGS. 9A and 9B. The processes shown in FIGS. 9A and 9B include the following: Storage/Parking providers sends shipment of RFID-tagged products with Unique Data to Inventory Location (block 901); Clerk receives shipment with bump transaction and SaaS updates inventory location with unique products (block 902); SaaS updates inventory location with unique products (block 921); Customer checks-in at storage/parking stock location with bump action to retailer location RFID tag (block 903); Customer creates unique event & bump product usage using NFC-enabled device (block 904); SaaS decrements inventory location for unique products as Customer stores/parks (block 921); continuation to FIG. 9B (block 922, 909, 910); complete trackable storage/parking event (block 922); Saas matches bumped products against catalog master for ePedigree reporting (block 909); SaaS generates Customer Bill for bumped Items with Item Price (block 910); SaaS adds Reward to Customer Bill based on Rewards business rules (block 912); Customer reviews and approves Bill with earned Rewards (block 923) and uses NFC payment option (block 200, 201, 215, 216); Clerk accepts payment and SaaS routes Trackable Event Bill data to legacy accounting system (block 202, 217, 223, 911); SaaS reports Trackable Event data to authorized users (block 916); Customer has access to Trackable Event product data (block 917); Provider has access to Trackable Event product data (block 918); Access to Trackable Event Item data in SaaS global registry (block 919); and access to Trackable Event product data in SaaS global registry (block 920).

UHF Tag and UHF Sensor Reader

Figure 10:
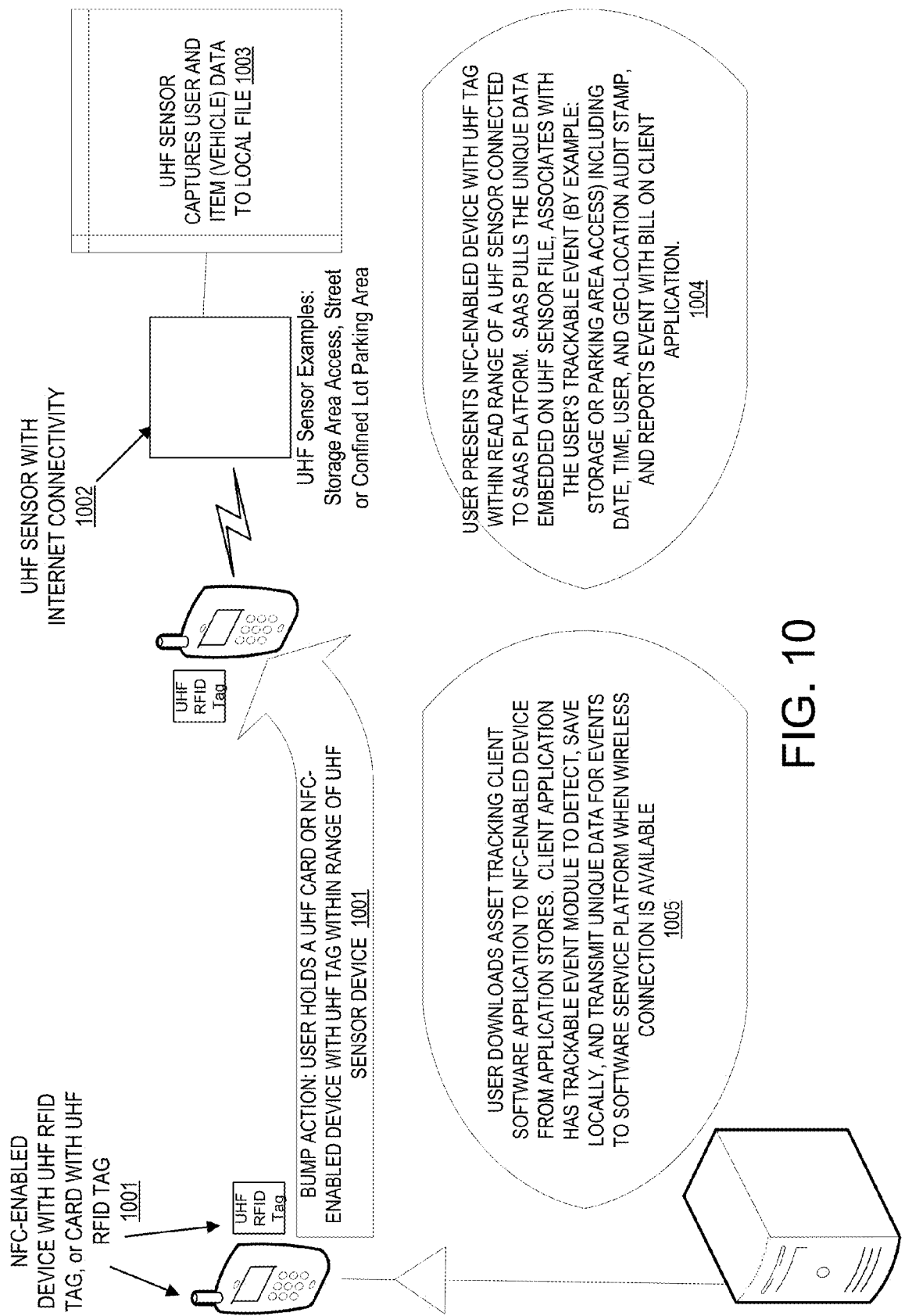
FIG. 10 is a schematic diagram of a transaction with a UHF tag and UHF sensor reader.

An Individual (e.g. Customer) may have a UHF tag embedded on their NFC-enabled device or on a plastic card (block 1001). The User may hold the NFC-enable device or card within the read range of a UHF sensor (block 1002) installed at a specific location. The UHF sensor, which may have a read range of many feet, shall recognize and record the User's UHF tag with User's Unique Data (user identification code, user name, blinded social security number (such as last four digits) and other unique identification information) and will initiate a new Trackable Event (FIG. 9A, block store the Trackable Event data on a local file (block 1003). The Service will import real-time any new Trackable Event Data from the UHF Sensor file to the remotely-hosted software as service platform to manage the User Trackable Event (block 202) and report the Trackable Event activity to the User and other interested stakeholders such as the Storage/Parking Provider (block 1004, FIG. 10, blocks 916,917,918,920). The User may complete the Trackable Event by passing within the UHF sensor read range with the NFC-enabled device or card holding the UHF tag (block (1000). The Service will repeat the read, store, and send to SaaS platform process to complete the Trackable Event (block 1004; FIG. 9B, block 922) and generate a Customer Bill based on the business rules established by the Storage/Parking Provider in the SaaS platform (block 910). The SaaS presents the Customer the Bill for the Trackable Event on their NFC-enabled device (block 923). The Customer can review, approve payment, and make notation of the Trackable Event type or definition and submit to the SaaS Service (block 923). The Service shall then route the approved payment to the Provider financial reporting system as well as the Customer's pre-designated expense management software as service vendor account for expense management and reporting purposes (block 217, 223) block 911). The Customer and Storage/Parking provider both have access to Trackable Event data as well as real-time availability of storage/parking availability based on other customer's use of the Service (block 916, 917, 918, 919).

Suitable Circuitry for NFC-Enabled Electronic Devices

A suitable NFC-enabled device may include, for example, a processor, processor-readable medium, a user interface, a NFC reader, and power circuitry, and optionally may include local input/output ("I/O") circuitry, motion detection circuitry, positioning circuitry, camera circuitry, telephony circuitry such as circuitry for cellular network access, and network communications circuitry, in any suitable combination of hardware, firmware and software.

A suitable processor includes processing or control circuitry operative to control device operations and performance, including the running of an operating system, utilities and applications, including operating system applications, firmware applications, media playback applications, media editing applications, or any other application. A processor may be implemented as a separate processor unit, or as a multi-core unit or multiple processor units, or as an integral part of a larger circuit such as the processor circuitry of a controller, or part of a system such as a computer system. In a computer system, processor-readable medium may be considered to be computer-readable medium.

Processor-readable medium includes memory such as, for example, digital storage media such as hard-drives, solid state drives, flash memory, permanent memory such as ROM, random access memory such as static random access memory and dynamic random access memory, cache memory, volatile memory, nonvolatile memory, and so forth, individually and in any combination. The material stored in memory for execution by the processor may be applications or data, and includes the operating system, utilities, applications, music and video files, application data, status data, firmware, user preference information data, authentication information, transaction information, wireless connection information, subscription information, contact information, security information, workout information, calendar information, and any other suitable data or any combination thereof. Memory may be implemented as a separate component, or may be physically integrated with a processor or otherwise into the device.

The user interface provides communication between the device and the user, either from the user to the device, or from the device to the user, or both. Suitable user interfaces include keyboards and keypads, buttons, dials, click wheels, touch pads, touch screens, microphones, display screens, speakers, audio input and output ports, motion detectors, and facial recognition, for example.

The NFC reader circuitry is described elsewhere in this document.

The power circuitry may require an external power source, or may include a portable source such as a battery, super capacitor, or kinetics.

Network communications circuitry includes any suitable communications circuitry for communicating over one or more networks. Suitable communications protocols include, for example, Wi-Fi (e.g., a 802.11 protocol), Bluetooth, radio frequency systems (e.g., 900 MHz, 1.4 GHz, and 5.6 GHz communication systems), infrared, GSM, GSM plus EDGE, CDMA, quadband, and other cellular protocols, VOIP, or any other suitable protocol.

The NFC-enabled device may be portable or stationary. A portable device may be small enough to be held in the hand of the user or may be larger but still able to be carried by the user. Suitable small portable devices include mobile digital devices, smartphones, full feature phones, cellular telephones, digital media players, personal e-mail devices, personal data assistants, handheld gaming devices, digital cameras, and so forth. Suitable large portable devices include tablets and laptops.

The methods described herein may be embodied in an application, which is one or more computer programs that reside on machine readable media. An application may have various components, including programs, sections of programs, subroutines, objects, collections of objects, API's, libraries, modules, and so forth. The machine readable media may be internally integrated in the device, or coupled to the device through physical ports such as USB and eSATA ports, memory card ports, and CDROM drives, or coupled to the device via wireless ports. The computer programs of the application may be fully contained on one such machine readable medium, or distributed across two or more such machine readable media.

The description of the invention including its applications and advantages as set forth herein is illustrative and is not intended to limit the scope of the invention. Variations and modifications of the embodiments disclosed herein are possible, and practical alternatives to and equivalents of the various elements of the embodiments would be known to one of ordinary skill in the art upon a study of this patent document. Moreover, unless otherwise stated any values provided herein are approximations, as would be appreciated by one of ordinary skill in the art. These and other variations and modifications of the embodiments disclosed herein, including of the alternatives and equivalents of the various elements of the embodiments, may be made without departing from the scope and spirit of the invention.

The invention claimed is:

1. A method of operating a Software as a Service ("SaaS") platform to furnish stakeholders with information about a plurality of trackable events, each involving one or more trackable items respectively associated with one or more RFID tags, comprising:
   providing a client software application for installation to a NFC-enabled device to acquire unique data corresponding to the trackable items and the trackable events, the trackable events being evidenced by respective bump actions between the NFC-enabled device and the one or more RFID tags at specific geo-locations, the unique data corresponding to the trackable items comprising unique RFID codes from the RFID tags, other data relating to the trackable items, or both, and the unique data corresponding to the trackable events comprising date, time and geo-location data coincident with the trackable events as determined by the NFC-enabled device;
   establishing secure transmissions between the SaaS platform and the NFC-enabled device over a network;
   receiving with the SaaS platform from the NFC-enabled device over the network via the secure transmissions, the unique data corresponding to the trackable events and the unique data corresponding to the trackable items;
   establishing on the SaaS platform a plurality of unique data items comprising the unique data corresponding to the trackable events and the unique data corresponding to the trackable items received with the SaaS platform in the receiving step;
   authenticating pedigrees of the trackable items through associations of the unique items back to respective product activation dates, with the SaaS platform and from the unique data corresponding to the trackable items;
   preparing on the SaaS platform from the unique data items different forms of reporting content for a plurality of different groups of entities and roles by entity having different uses for the reporting content; and
   furnishing from the SaaS platform the different forms of reporting content respectively to the entities and roles by entity.

2. The method of claim 1 wherein the trackable events comprise asset tracking events associated with entities comprising Facility, Manufacturer, User, Order Issuer, Order Approver/Payer, Rewards Manager, or any combination of the foregoing, and the roles by entity comprise Scheduler, Inventory Control Person, Manager for Facility, Sales Representative and Distributor for Manufacturer, User and Associates for User, Order Issuer and Scheduler for Order Issuer, Approver and Claim Payer for Payer, Administrator and Account Manager for Rewards Manager, or any combination of the foregoing.

3. The method of claim 1 wherein the trackable events comprise order adherence events associated with entities comprising Company, Manufacturer, Retail, Order Issuer, Customer, RFID Vendor, Payer, or any combination of the foregoing, and the roles by entity comprise Production Manager for Company, Production Manager for Manufacturer, Order Fulfillment for Retail, Individual and Associates for Customer, Order Issuer for Order Issuer, Order Approver for Payer, or any combination of the foregoing.

4. The method of claim 2 wherein the trackable events further comprise order adherence events associated with entities comprising Company, Manufacturer, Retail, Order Issuer, Customer, RFID Vendor, Payer, or any combination of the foregoing, and the roles by entity further comprise Production Manager for Company, Production Manager for Manufacturer, Order Fulfillment for Retail, Individual and Associates for Customer, Order Issuer for Order Issuer, Order Approver for Payer, or any combination of the foregoing.

5. The method of claim 1 further comprising:
determining completion by an individual user of the trackable events;
calculating an earned reward based on the individual user completion of the trackable events; and
furnishing the earned reward or a notification thereof to the NFC-enabled device.

6. The method of claim 4 further comprising:
determining completion by an individual user of the trackable events;
calculating an earned reward based on the individual user completion of the trackable events; and
furnishing the earned reward or a notification thereof to the NFC-enabled device.

7. The method of claim 6 wherein the earned reward has a value, further comprising:
administering deduction of the value of the earned reward against an obligation of the individual user; and
reporting the deduction to the individual user.

8. The method of claim 1 wherein the unique data receiving step, the reporting content preparing step, and the reporting content furnishing step are performed within a time established by customary digital processing delays and cloud latency.

9. The method of claim 5 wherein the earned reward has a value, further comprising:
administering deduction of the value of the earned reward against an obligation of the individual user; and
reporting the deduction to the individual user.

10. The method of claim 5 wherein the unique data receiving step, the reporting content preparing step, and the reporting content furnishing step are performed within a time established by customary digital processing delays and cloud latency.

11. The method of claim 6 wherein the unique data receiving step, the reporting content preparing step, and the reporting content furnishing step are performed within a time established by customary digital processing delays and cloud latency.

12. The method of claim 1 further comprising:
determining information on completion and non-completion by an individual user of the trackable events based on an order schedule; and
including the completion and non-completion information in the reporting content.

13. A software as a service ("SaaS") platform comprising:
a processor;
a memory coupled to the processor, the memory storing processor-executable instructions in one or more programs to perform a method of furnishing stakeholders with information about a plurality of trackable events, each involving one or more trackable items respectively associated with one or more RFID tags, the instructions comprising:
instructions for providing a client software application for installation to a NFC-enabled device to acquire unique data corresponding to the trackable items and the trackable events, the trackable events being evidenced by respective bump actions between the NFC-enabled device and the one or more RFID tags at specific geo-locations, the unique data corresponding to the trackable items comprising unique RFID codes from the RFID tags, other data relating to the trackable items, or both, and the unique data corresponding to the trackable events comprising date, time and geo-location data coincident with the trackable events as determined by the NFC-enabled device;
instructions for establishing secure transmissions between the SaaS platform and the NFC-enabled device over a network;
instructions for receiving from the NFC-enabled device over the network via the secure transmissions, the unique data corresponding to the trackable events and the unique data corresponding to the trackable items;
instructions for establishing a plurality of unique data items comprising the unique data corresponding to the trackable events and the unique data corresponding to the trackable items received in accordance with the receiving instructions;
instructions for authenticating pedigrees of the trackable items through associations of the unique items back to respective product activation dates, with the SaaS platform and from the unique data corresponding to the trackable items;
instructions for preparing from the unique data items different forms of reporting content for a plurality of different groups of entities and roles by entity having different uses for the reporting content; and
instructions for furnishing the different forms of reporting content respectively to the entities and roles by entity.

14. The SaaS platform of claim 13 wherein the instructions further comprise:
instructions for determining information on completion and non-completion by an individual user of the trackable events based on an order schedule; and
instructions for including the completion and non-completion information in the reporting content.

* * * * *